US012599406B2

(12) United States Patent
Davies et al.

(10) Patent No.: US 12,599,406 B2
(45) Date of Patent: *Apr. 14, 2026

(54) METHODS AND DEVICES FOR PUNCTURING TISSUE

(71) Applicant: Boston Scientific Medical Device Limited, Galway (IE)

(72) Inventors: Gareth Davies, Toronto (CA); John Paul Urbanski, Toronto (CA); Ferryl Alley, Devonshire (BM); Bogdan Beca, Thornhill (CA)

(73) Assignee: Boston Scientific Medical Device Limited, Galway (IE)

( * ) Notice: Subject to any disclaimer, the term of this patent is extended or adjusted under 35 U.S.C. 154(b) by 0 days.

This patent is subject to a terminal disclaimer.

(21) Appl. No.: 19/270,234

(22) Filed: Jul. 15, 2025

(65) Prior Publication Data

US 2025/0339179 A1 Nov. 6, 2025

Related U.S. Application Data

(63) Continuation of application No. 19/007,196, filed on Dec. 31, 2024, now Pat. No. 12,433,639, which is a
(Continued)

(51) Int. Cl.
*A61B 18/14* (2006.01)
*A61B 17/34* (2006.01)
(Continued)

(52) U.S. Cl.
CPC ...... *A61B 17/3478* (2013.01); *A61B 18/1492* (2013.01); *A61B 90/39* (2016.02);
(Continued)

(58) Field of Classification Search
CPC ...... A61B 18/1492; A61B 2018/00351; A61B 2018/00363; A61B 2018/00601;
(Continued)

(56) References Cited

U.S. PATENT DOCUMENTS 175,254 A 3/1876 Oberly
827,626 A 7/1906 Gillet
(Continued)

FOREIGN PATENT DOCUMENTS

EP 0465449 A2 1/1992
EP 2444115 A1 4/2012
(Continued)

OTHER PUBLICATIONS

Defendant Atraverse Medical, Inc.'s Answer to the Amended Complaint and Counterclaims, *Boston Scientific Corporation and Boston Scientific Medical Device Limited* v. *Atraverse Medical, Inc.*, Case No. CA. No. 25-1035, in the United States District Court for the District of Delaware, filed Nov. 10, 2025.
(Continued)

*Primary Examiner* — Michael F Peffley
(74) *Attorney, Agent, or Firm* — Nelson Mullins Riley & Scarborough LLP

(57) ABSTRACT

Novel and unique medical devices and associated methods are disclosed, for a medical device for puncturing tissue at a tissue site. The medical device includes an elongate member having a distal section defining a distal section curved portion and a distal section straight portion. The distal section straight portion is distal to the distal section curved portion. An active tip is located at a distal end of the distal section. The active tip is operable to deliver energy to create a puncture through the tissue. The medical device includes a constant diameter layer. The distal section straight portion includes a minimum diameter portion located proximal to a constant diameter portion, and the constant diameter layer surrounds the minimum diameter portion.

13 Claims, 23 Drawing Sheets

Related U.S. Application Data continuation of application No. 18/678,567, filed on May 30, 2024, which is a continuation of application No. 17/474,415, filed on Sep. 14, 2021, now Pat. No. 11,998,238, which is a continuation of application No. 16/445,790, filed on Jun. 19, 2019, now Pat. No. 11,154,324, which is a continuation of application No. 14/910,525, filed as application No. PCT/IB2013/060287 on Nov. 20, 2013, now Pat. No. 10,368,911.

(60) Provisional application No. 61/863,579, filed on Aug. 8, 2013, provisional application No. 61/863,265, filed on Aug. 7, 2013.

(51) Int. Cl.
| | |
|---|---|
| *A61B 90/00* | (2016.01) |
| *A61B 17/00* | (2006.01) |
| *A61B 17/22* | (2006.01) |
| *A61B 18/00* | (2006.01) |

(52) U.S. Cl.
CPC .............. *A61B 2017/00247* (2013.01); *A61B 2017/003* (2013.01); *A61B 2017/22042* (2013.01); *A61B 2017/3488* (2013.01); *A61B 2018/00351* (2013.01); *A61B 2090/3966* (2016.02)

(58) Field of Classification Search
CPC .......... A61B 2018/144; A61B 17/3478; A61B 2017/00247; A61B 2017/003; A61B 2017/22042; A61B 2017/22044; A61B 2017/3488; A61B 2090/3966; A61B 90/39; A61M 25/0041; A61M 25/09
See application file for complete search history.

(56) References Cited

U.S. PATENT DOCUMENTS

| | | | |
|---|---|---|---|
| 848,711 | A | 4/1907 | Weaver |
| 1,072,954 | A | 9/1913 | Junn |
| 1,279,654 | A | 9/1918 | Charlesworth |
| 1,918,094 | A | 7/1933 | Geekas |
| 1,996,986 | A | 4/1935 | Weinberg |
| 2,021,989 | A | 11/1935 | De Master |
| 2,146,636 | A | 2/1939 | Lipchow |
| 3,429,574 | A | 2/1969 | Williams |
| 3,448,739 | A | 6/1969 | Stark et al. |
| 3,575,415 | A | 4/1971 | Fulp et al. |
| 3,595,239 | A | 7/1971 | Petersen |
| 4,129,129 | A | 12/1978 | Amrine |
| 4,135,518 | A | 1/1979 | Dutcher |
| 4,244,362 | A | 1/1981 | Anderson |
| 4,401,124 | A | 8/1983 | Guess et al. |
| 4,458,695 | A | 7/1984 | Peers-Trevarton |
| 4,639,252 | A | 1/1987 | Kelly et al. |
| 4,641,649 | A | 2/1987 | Walinsky et al. |
| 4,669,467 | A | 6/1987 | Willett et al. |
| 4,682,596 | A | 7/1987 | Bales et al. |
| 4,790,311 | A | 12/1988 | Ruiz |
| 4,790,809 | A | 12/1988 | Kuntz |
| 4,793,350 | A | 12/1988 | Mar et al. |
| 4,807,620 | A | 2/1989 | Strul et al. |
| 4,811,743 | A | 3/1989 | Stevens |
| 4,832,048 | A | 5/1989 | Cohen |
| 4,840,622 | A | 6/1989 | Hardy |
| 4,863,441 | A | 9/1989 | Lindsay et al. |
| 4,884,567 | A | 12/1989 | Elliott et al. |
| 4,892,104 | A | 1/1990 | Ito et al. |
| 4,896,671 | A | 1/1990 | Cunningham et al. |
| 4,928,693 | A | 5/1990 | Goodin et al. |
| 4,936,281 | A | 6/1990 | Stasz |
| 4,951,677 | A | 8/1990 | Crowley et al. |

| | | | | | |
|---|---|---|---|---|---|
| 4,960,410 | A | | 10/1990 | Pinchuk | |
| 4,977,897 | A | | 12/1990 | Hurwitz | |
| 4,998,933 | A | | 3/1991 | Eggers et al. | |
| 5,006,119 | A | | 4/1991 | Acker et al. | |
| 5,019,076 | A | | 5/1991 | Yamanashi et al. | |
| 5,047,026 | A | | 9/1991 | Rydell | |
| 5,067,489 | A | | 11/1991 | Lind | |
| 5,081,997 | A | | 1/1992 | Bosley et al. | |
| 5,098,392 | A | | 3/1992 | Fleischhacker et al. | |
| 5,098,431 | A | | 3/1992 | Rydell | |
| 5,112,048 | A | | 5/1992 | Kienle | |
| 5,154,724 | A | | 10/1992 | Andrews | |
| 5,176,149 | A | | 1/1993 | Grenouillet | |
| 5,180,368 | A | | 1/1993 | Garrison | |
| 5,201,756 | A | | 4/1993 | Horzewski et al. | |
| 5,209,741 | A | | 5/1993 | Spaeth | |
| 5,211,183 | A | | 5/1993 | Wilson | |
| 5,221,256 | A | | 6/1993 | Mahurkar | |
| 5,230,349 | A | | 7/1993 | Langberg | |
| 5,281,216 | A | | 1/1994 | Klicek | |
| 5,300,068 | A | | 4/1994 | Rosar et al. | |
| 5,300,069 | A | | 4/1994 | Hunsberger et al. | |
| 5,312,341 | A | | 5/1994 | Turi | |
| 5,314,418 | A | | 5/1994 | Takano et al. | |
| 5,318,525 | A | | 6/1994 | West et al. | |
| 5,327,905 | A | | 7/1994 | Avitall | |
| 5,364,393 | A | | 11/1994 | Auth et al. | |
| 5,366,443 | A | * | 11/1994 | Eggers ................. | A61B 18/149 |
| | | | | | 604/114 |
| 5,372,596 | A | | 12/1994 | Klicek et al. | |
| 5,379,779 | A | | 1/1995 | Rowland et al. | |
| 5,380,304 | A | | 1/1995 | Parker | |
| 5,395,341 | A | | 3/1995 | Slater | |
| 5,397,304 | A | | 3/1995 | Truckai | |
| 5,403,338 | A | | 4/1995 | Milo | |
| 5,423,809 | A | | 6/1995 | Klicek | |
| 5,425,382 | A | | 6/1995 | Golden et al. | |
| 5,437,664 | A | | 8/1995 | Cohen et al. | |
| 5,490,859 | A | | 2/1996 | Mische et al. | |
| 5,497,774 | A | | 3/1996 | Swartz et al. | |
| 5,499,975 | A | | 3/1996 | Cope et al. | |
| 5,507,751 | A | | 4/1996 | Goode et al. | |
| 5,509,411 | A | | 4/1996 | Littmann et al. | |
| 5,540,681 | A | | 7/1996 | Strul et al. | |
| 5,545,200 | A | | 8/1996 | West et al. | |
| 5,555,618 | A | | 9/1996 | Winkler | |
| 5,571,088 | A | | 11/1996 | Lennox et al. | |
| 5,575,766 | A | | 11/1996 | Swartz et al. | |
| 5,575,772 | A | | 11/1996 | Lennox | |
| 5,582,609 | A | | 12/1996 | Swanson et al. | |
| 5,599,347 | A | | 2/1997 | Hart et al. | |
| 5,605,162 | A | | 2/1997 | Mirzaee et al. | |
| 5,617,878 | A | | 4/1997 | Taheri | |
| 5,622,169 | A | | 4/1997 | Golden et al. | |
| 5,624,430 | A | | 4/1997 | Eton et al. | |
| 5,655,548 | A | | 8/1997 | Nelson et al. | |
| 5,664,580 | A | | 9/1997 | Erickson et al. | |
| 5,666,968 | A | | 9/1997 | Imran et al. | |
| 5,667,488 | A | | 9/1997 | Lundquist et al. | |
| 5,673,695 | A | | 10/1997 | Mcgee et al. | |
| 5,674,208 | A | | 10/1997 | Berg et al. | |
| 5,680,860 | A | * | 10/1997 | Imran ................. | A61B 18/1492 |
| | | | | | 606/41 |
| 5,683,366 | A | | 11/1997 | Eggers et al. | |
| 5,720,744 | A | | 2/1998 | Eggleston et al. | |
| 5,722,425 | A | | 3/1998 | Bostrom | |
| 5,741,249 | A | | 4/1998 | Moss et al. | |
| 5,766,135 | A | | 6/1998 | Terwilliger | |
| 5,779,688 | A | | 7/1998 | Imran et al. | |
| 5,810,764 | A | | 9/1998 | Eggers et al. | |
| 5,814,028 | A | | 9/1998 | Swartz et al. | |
| 5,830,214 | A | | 11/1998 | Flom et al. | |
| 5,836,875 | A | | 11/1998 | Webster, Jr. | |
| 5,849,011 | A | | 12/1998 | Jones et al. | |
| 5,851,210 | A | | 12/1998 | Torossian | |
| 5,885,227 | A | | 3/1999 | Finlayson | |
| 5,888,201 | A | | 3/1999 | Stinson et al. | |
| 5,893,848 | A | | 4/1999 | Negus et al. | |
| 5,893,885 | A | | 4/1999 | Webster, Jr. | |

(56) References Cited

U.S. PATENT DOCUMENTS

| | | | |
|---|---|---|---|
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,944,701 A | 8/1999 | Dubrul |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,971,983 A | 10/1999 | Lesh |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,036,677 A | 3/2000 | Javier, Jr. et al. |
| 6,047,700 A | 4/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,123,718 A | 9/2000 | Tu et al. |
| 6,139,540 A | 10/2000 | Rost et al. |
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,200,315 B1 | 3/2001 | Gaiser et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,325,797 B1 * | 12/2001 | Stewart .............. A61B 18/1492 |
| | | 606/41 |
| 6,328,699 B1 | 12/2001 | Eigler et al. |
| 6,360,128 B2 | 3/2002 | Kordis et al. |
| 6,364,877 B1 | 4/2002 | Goble et al. |
| 6,371,955 B1 | 4/2002 | Fuimaono et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Dubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |

| | | | |
|---|---|---|---|
| 6,565,562 B1 | 5/2003 | Shah et al. |
| 6,607,520 B2 | 8/2003 | Keane |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,165,552 B2 | 1/2007 | Deem et al. |
| 7,186,251 B2 | 3/2007 | Malecki et al. |
| 7,316,656 B2 | 1/2008 | Shireman et al. |
| 7,335,197 B2 | 2/2008 | Sage et al. |
| 7,618,430 B2 | 11/2009 | Scheib |
| 7,621,880 B2 | 11/2009 | Ryan et al. |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,715,903 B2 | 5/2010 | Hartley et al. |
| 7,824,345 B2 | 11/2010 | Euteneuer et al. |
| 7,828,796 B2 | 11/2010 | Wong et al. |
| 7,900,928 B2 | 3/2011 | Held et al. |
| 7,988,690 B2 | 8/2011 | Chanduszko et al. |
| 7,993,287 B2 | 8/2011 | Haller |
| 8,021,359 B2 | 9/2011 | Auth et al. |
| 8,092,450 B2 | 1/2012 | Davies et al. |
| 8,096,959 B2 | 1/2012 | Stewart et al. |
| 8,182,432 B2 | 5/2012 | Kim et al. |
| 8,192,425 B2 | 6/2012 | Mirza et al. |
| 8,235,916 B2 | 8/2012 | Whiting et al. |
| 8,257,323 B2 | 9/2012 | Joseph et al. |
| 8,277,469 B2 | 10/2012 | Carmeli et al. |
| 8,337,518 B2 | 12/2012 | Nance et al. |
| 8,360,995 B2 | 1/2013 | Elsesser et al. |
| 8,388,549 B2 | 3/2013 | Paul et al. |
| 8,417,332 B2 | 4/2013 | Ollivier |
| 8,500,697 B2 | 8/2013 | Kurth et al. |
| 8,622,934 B2 | 1/2014 | Muzslay et al. |
| 8,721,633 B2 | 5/2014 | Warnking et al. |
| 8,968,175 B2 | 3/2015 | Annest et al. |
| 9,510,900 B2 | 12/2016 | Abou-Marie et al. |
| 9,597,146 B2 * | 3/2017 | Davies ............... A61B 18/1492 |
| 10,314,541 B2 | 6/2019 | Hilmersson |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2001/0044591 A1 | 11/2001 | Stevens et al. |
| 2002/0019644 A1 | 2/2002 | Hastings et al. |
| 2002/0022781 A1 | 2/2002 | McIntire et al. |
| 2002/0022836 A1 | 2/2002 | Goble et al. |
| 2002/0035361 A1 | 3/2002 | Houser et al. |
| 2002/0066450 A1 | 6/2002 | Bonutti |

(56) References Cited

U.S. PATENT DOCUMENTS

| | | |
|---|---|---|
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0208220 A1 | 11/2003 | Worley et al. |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0167436 A1 | 8/2004 | Reynolds et al. |
| 2004/0167440 A1 | 8/2004 | Sharrow |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0038359 A1 | 2/2005 | Aimi et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0065588 A1 | 3/2005 | Zhao et al. |
| 2005/0085806 A1 | 4/2005 | Auge et al. |
| 2005/0096529 A1 | 5/2005 | Cooper et al. |
| 2005/0101984 A1* | 5/2005 | Chanduszko ...... A61B 17/0057 |
| | | 606/185 |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0185522 A1 | 8/2007 | Davies et al. |
| 2007/0208256 A1 | 9/2007 | Marilla |
| 2007/0225681 A1 | 9/2007 | House |
| 2007/0270741 A1 | 11/2007 | Hassett et al. |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0243222 A1 | 10/2008 | Schafersman et al. |
| 2008/0275439 A1 | 11/2008 | Francischelli et al. |
| 2009/0093802 A1 | 4/2009 | Kulesa et al. |
| 2009/0105654 A1 | 4/2009 | Kurth et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0182281 A1 | 7/2009 | Kurth et al. |
| 2009/0264977 A1 | 10/2009 | Bruszewski et al. |
| 2010/0022948 A1 | 1/2010 | Wilson et al. |
| 2010/0087789 A1 | 4/2010 | Leeflang et al. |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0228330 A1 | 9/2010 | Bornzin |
| 2010/0249491 A1 | 9/2010 | Farnan et al. |
| 2011/0046619 A1 | 2/2011 | Ducharme |
| 2011/0130752 A1 | 6/2011 | Ollivier |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2011/0224666 A1 | 9/2011 | Davies et al. |
| 2012/0095448 A1 | 4/2012 | Kajii |
| 2012/0109079 A1 | 5/2012 | Asleson et al. |
| 2012/0232546 A1 | 9/2012 | Mirza et al. |
| 2012/0265055 A1 | 10/2012 | Melsheimer et al. |
| 2012/0296262 A1 | 11/2012 | Ogata et al. |
| 2012/0330156 A1 | 12/2012 | Brown et al. |
| 2013/0006222 A1 | 1/2013 | Nabeshima et al. |
| 2013/0025588 A1 | 1/2013 | Bosel |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0012228 A1 | 1/2014 | Jabba et al. |
| 2014/0188108 A1 | 7/2014 | Goodine et al. |
| 2014/0206987 A1 | 7/2014 | Urbanski et al. |
| 2014/0296769 A1 | 10/2014 | Hyde et al. |
| 2015/0173782 A1 | 6/2015 | Garrison et al. |
| 2015/0245882 A1 | 9/2015 | Venkatraghavan et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| EP | 2550988 A1 | 1/2013 |
| JP | 60-261465 A | 12/1985 |
| JP | 2007-510458 A | 4/2007 |
| JP | 2009-537255 A | 10/2009 |
| JP | 2010-227580 A | 10/2010 |
| WO | 2005/065562 A1 | 7/2005 |
| WO | 2008/066557 A1 | 6/2008 |
| WO | 2008/079828 A2 | 7/2008 |
| WO | 2011/014496 A1 | 2/2011 |
| WO | 2013/101632 A1 | 7/2013 |

OTHER PUBLICATIONS

Examination Report issued in Australian Patent Application No. 2013397477, dated May 11, 2018, 5 pages.
Plaintiff Boston Scientific Corporation and Boston Scientific Medical Device Limited Amended Complaint for Patent Infringement, Case No. 25-cv-1035-JLH, U.S. District Court for the District of Delaware, dated Oct. 9, 2025.
Plaintiff Boston Scientific Corporation and Boston Scientific Medical Device Limited's Answer to Defendant Atraverse Medical Inc.'s Counterclaims, Case No. 25-cv-1035-JLH, U.S. District Court for the District of Delaware, dated Dec. 1, 2025.

(56) References Cited

OTHER PUBLICATIONS

European Search Opinion for European Application No. 13891200.1 dated Feb. 7, 2017.
International Search Report and Written Opinion received for PCT Patent Application No. PCT/IB2013/060287, mailed on Mar. 6, 2014, 16 pages.
Japanese Patent Office Examination Report for counterpart Japanese Application No. 2016-532745, dated Oct. 3, 2017.
Search Report for corresponding European patent application EP19204215.
Search Report for corresponding Japanese patent application 2018211611.
Supplementary European Search Report for European Application No. 13891200.1 dated Feb. 7, 2017.
Office Action for U.S. Appl. No. 19/362,162 mailed Feb. 11, 2026. 11 pages.

* cited by examiner

METHODS AND DEVICES FOR PUNCTURING TISSUE

CROSS REFERENCE TO RELATED APPLICATIONS

The present application is a continuation of U.S. application Ser. No. 19/007,196, filed Dec. 31, 2024, which is a continuation of U.S. application Ser. No. 18/678,567, filed May 30, 2024, which is a continuation of U.S. application Ser. No. 17/474,415, filed Sep. 14, 2021, now issued as U.S. Pat. No. 11,998,238, which is a continuation of U.S. application Ser. No. 16/445,790, filed on Jun. 19, 2019, now issued as U.S. Pat. No. 11,154,324, which is a continuation of U.S. application Ser. No. 14/910,525, filed on Feb. 5, 2016, now issued as U.S. Pat. No. 10,368,911, which is a national phase entry of PCT/IB2013/060287, filed on Nov. 20, 2013, which claims benefit of U.S. application 61/863,265, filed on Aug. 7, 2013 and claims benefit of U.S. application 61/863,579 filed on Aug. 8, 2013. The disclosures of each of the foregoing applications are hereby incorporated by reference in their entirety for all purposes.

TECHNICAL FIELD

The disclosure relates to devices, systems and methods used to gain access to various tissue sites from particular access sites, and in particular to devices and associated methods used to access the left side of a heart via puncturing tissue.

SUMMARY OF THE DISCLOSURE

In one broad aspect, embodiments of the present invention comprise a medical device for puncturing tissue at a tissue site. The medical device is an elongate member having a proximal section, a distal section, and a rail section therebetween. The medical device includes an active tip at a distal end of the distal section and is operable to deliver energy to create a puncture through the tissue. The rail section is configured to both act as a rail for supporting installation of one or more tubular members thereupon, as well as be maneuverable for enabling access to the tissue site.

In the aforementioned embodiments, the distal section defines a distal section curved portion and a distal section straight portion, where the distal section straight portion is distal to the distal section curved portion. A further embodiment of the present invention has the elongate member comprising a reverse taper. The reverse taper increases in outer diameter from the distal end of the distal section curved portion to the distal section straight portion. In an embodiment of the present invention, the distal section defines a distal section curved portion configured to automatically form a distal coil in a deployed state for anchoring the distal section upon the distal section being advanced through the puncture. Further, the coil is configured such that, upon deployment from a confined state, along an axis of advancement, the active tip curves away from the axis of advancement. Additionally, the distal section further comprises a distal section straight portion, distal to the distal section curved portion. The distal section straight portion includes the active tip. In some embodiments, the distal section straight portion has a length of about 3 mm to 10 mm. In some embodiments, the distal coil is configured as a double pigtail curve. In another embodiment of the present invention, the elongate member is a conductive guidewire.

The electrically conductive guidewire is substantially covered by a layer of electrical insulation with a distal tip of the electrically conductive guidewire exposed. Further, the guidewire comprises an exposed portion on the proximal section for coupling to a source of electrical energy. In some embodiments, the active tip is substantially atraumatic. In some embodiments, the medical device includes a radiopaque marker positioned on the distal section. In another embodiment, the radiopaque marker comprises a helical coil around the elongate member at the distal section. In some embodiments, the active tip comprises an electrode. Further, the electrode is dome shaped.

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1:
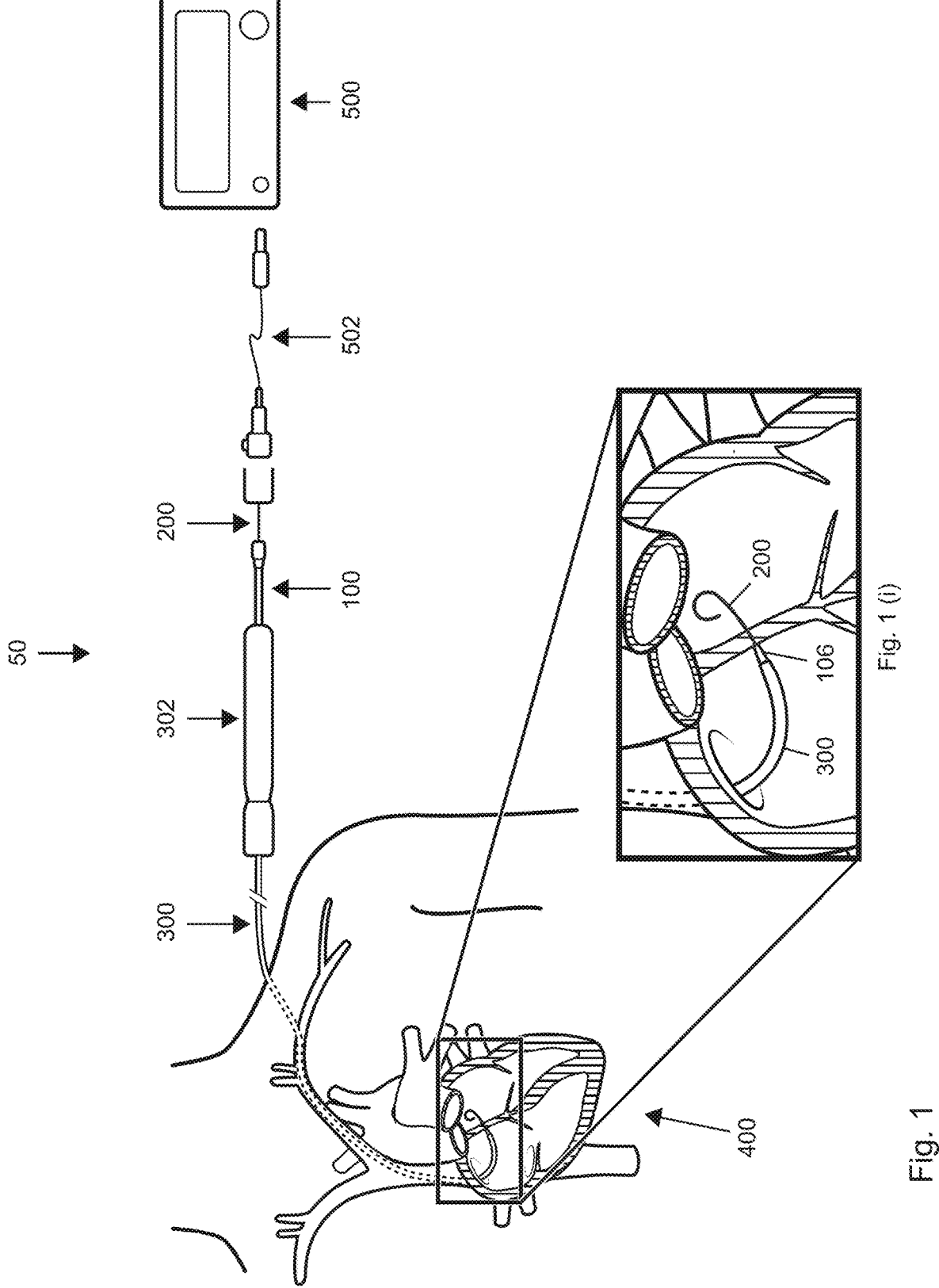
FIG. 1 is an illustration of a system in accordance with an embodiment of the present invention.

In some medical applications, it may be desirable to reach a desired target tissue site within a region of tissue within a patient's body in order for example, to provide access to a particular cavity or space. In some applications access to the cavity or space may be provided through a puncture that is created within the desired tissue site. In order to initially reach the desired tissue site within the region of tissue, access may be provided into and/or through vasculature using a guidewire. A sheath and dilator assembly may then be advanced over the guide wire, and the sheath may be used to guide the dilator, as well as any other devices positioned through the assembly, to the desired target tissue site.

In some such applications, a particular access point into the patient's vasculature may be dictated by, for example, treatment requirements or anatomical considerations. For example, patients with occluded or stenosed vasculature may require an alternate access point. In addition, procedures such as lead placement dictate particular access points in order to allow implanted leads to be connected to a battery.

Thus, in certain procedures, a particular tissue puncture site is required while the access point into the vasculature is also restricted. In some such procedures, delivering treatment tools and assemblies from the access point to the tissue puncture site is difficult and/or may require many device exchanges due, for example, to the curvature and/or tortuosity of the vasculature within that region of the body.

For example, in some such applications, a very sharp or high curve or trajectory may be required to access the desired tissue site. In order to reach the desired tissue site, fixed curve sheaths or steerable sheaths may be utilized but both have drawbacks when used with current accessory devices.

In particular, where a fixed curve sheath is used, the fixed curve sheath may not be able to retain its curvature. This may be a result of a relatively stiff dilator and/or other devices inserted within the fixed curve sheath. As such, the sheath may not be able to position the dilator and/or any other device at the desired target tissue site.

In situations where a steerable sheath is utilized, upon actuation of the steerable sheath (in some such embodiments), the stiffness of the dilator, and/or any additional devices inserted through the steerable sheath, may limit or prevent the steerable sheath from reaching the intended or required curvature, thus preventing the steerable sheath from positioning the dilator and/or other devices at the target tissue site. Furthermore, stiffness of the dilator may result in breakage of the actuation mechanism of the steerable sheath upon actuation of the steerable sheath. In one particular example, the pull wires may separate from a distal joint within the sheath or may separate from the proximal lever or actuation mechanism of the steerable sheath. In other examples, the stiffness of the dilator may result in breakage of the pull wires upon actuation of the steerable sheath.

In addition, as mentioned above, puncturing certain tissue sites while being limited to particular access points also often requires exchanging devices multiple times, with each device performing a specific function during the course of the procedure. For example, current methods of accessing a heart chamber on the left side of the heart using a superior access approach require multiple device exchanges resulting in relatively inefficient and lengthy procedures. In a further example of procedural inefficiencies, existing techniques for gaining transseptal access for delivery of cardiac leads generally require that the transseptal puncture and lead delivery be performed using different access points, necessitating, for example, either transferring the lead, or trying to re-locate the puncture site, and then installing the lead within the heart.

The present inventors have conceived and reduced to practice novel and unique devices (which may be referred to as "hybrid devices" in the description below) and associated methods to facilitate efficient and repeatable puncture of a plurality of tissue sites while allowing vascular access from various access points on a patient's body. These devices include dilators and wires, for example guidewires, usable alone or in combination to facilitate this tissue access and puncture at various anatomical locations from desired access points.

For example, the present inventors have conceived and reduced to practice a flexible dilator that is usable in combination with an ancillary medical device (which may include a catheter, a fixed curve sheath or a steerable sheath), the dilator being designed and configured so that it does not substantially affect the curvature of the ancillary device.

Embodiments of a dilator of the present invention are sufficiently flexible to allow the ancillary device to guide and position the dilator and/or additional devices in a wide array of patient anatomies. Embodiments of the dilator accomplish this function by providing a flexible intermediate region having reduced stiffness. The location of the flexible region, when the dilator is inserted into/through the ancillary device, corresponds to a region of the ancillary device that is amenable to deflection or has a particular shape or curve, whereby the flexibility of the dilator at that location helps to ensure that the dilator does not substantially impair the ability of the ancillary device to retain, maintain or reach its intended shape or curvature. In some embodiments, the dilator, while being sufficiently flexible along the intermediate region, has sufficient stiffness along a distal end region to allow the dilator to be tracked or advanced across tissue for dilating a perforation or puncture at the desired target tissue site.

Relatedly, the present inventors have discovered, and reduced to practice, guidewire-based medical devices for puncturing a septum of the heart and for providing reliable and robust guidewire rail support across the puncture even when accessing the heart via veins superior to the heart (such as the subclavian veins). Such medical devices are sufficiently flexible to be directed towards the appropriate puncture site from the desired access point, yet are also stiff enough to support insertion of additional devices thereupon. In addition, embodiments of such devices include features for maintaining the medical device in position across the puncture to maintain patency of the puncture and to ensure continued access to tissue across the puncture.

Furthermore, the present inventors have conceived and reduced to practice methods of treatment that employ one or more novel devices for puncturing tissue sites utilizing defined access points and for performing multiple steps of the procedure to thereby reduce and/or minimize the number of device exchanges. In addition to improving efficiencies and reducing treatment procedure time, these methods allow for transseptal puncture and lead delivery to be performed using a single access point.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Systems

FIG. 1 is an illustration of a system 50 that incorporates embodiments of devices of the present invention and that may be utilized during the course of an inventive procedure as described further hereinbelow. As illustrated, system 50 includes a steerable device such as steerable sheath 300 with dilator 100 inserted therein, and wire 200 inserted into dilator 100. Steerable sheath 300 and dilator 100 each defines a respective lumen through which devices may be inserted, and may therefore be referred to as "tubular members". Although a steerable sheath is discussed throughout this application, it will be evident to one of skill in the art that other steerable devices or articulating components may be used. For ease of explaining the fundamental principles of the invention, "Steerable Sheath" will be used throughout the specification as an example of a steerable or articulating device. Alternatively, in some embodiments, a fixed curve sheath may be utilized in place of an articulating sheath, depending on the access point and tissue puncture site chosen by a user.

Wire 200 is connected to a generator 500 by connector 502. Steerable sheath 300 includes a steerable sheath handle 302. In some embodiments, the steerable sheath is unidirectional i.e. it allows deflection in a single direction. In other embodiments, a bi-directional sheath may be used. In the exemplary applications disclosed below, an 8.5 French steerable sheath with a 40 cm usable length is typically used; procedures for larger patients may use a sheath with a 45 cm usable length or other lengths as may be appropriate. FIG. 1(*i*) shows an expanded view of a portion of heart 400 illustrating a distal portion of steerable sheath 300, distal tip 106 of dilator 100, and wire 200, which may be a radiofrequency puncture wire.

Dilators

Figures 1A, 1B:
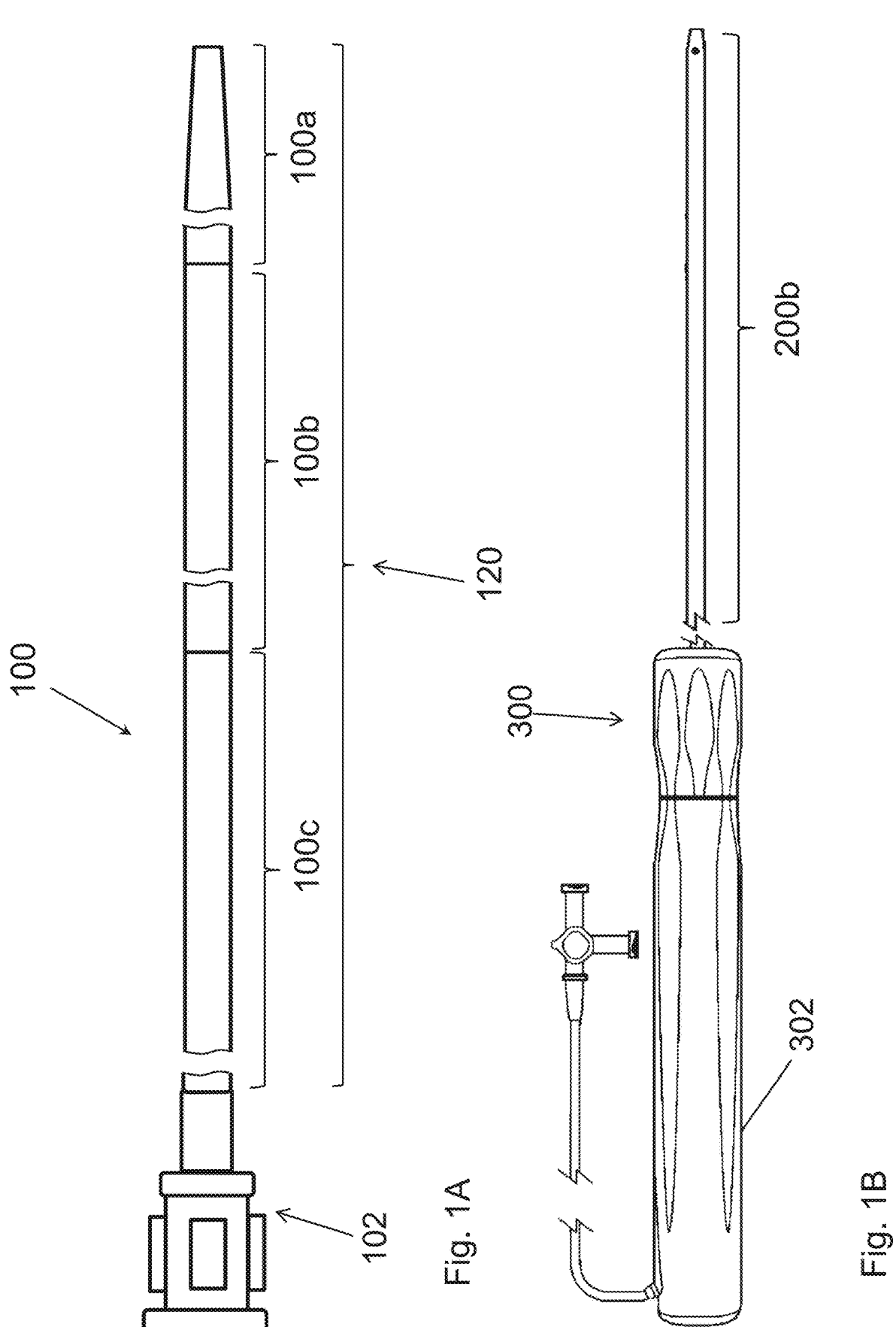
FIG. 1A is an illustration of a dilator in accordance an embodiment of the present invention.
FIG. 1B is an illustration of a steerable sheath for use with a dilator in accordance with an embodiment of the present invention.

In accordance with one embodiment of the present invention, as shown in FIG. 1A, a flexible dilator 100 is disclosed for use with a steerable sheath 300 (shown in FIG. 1B) to access a region of tissue within a patient's body. The steerable sheath 300 has a range of deflection angles and can achieve a range of curvatures upon actuation. Referring again to FIG. 1A, the dilator 100 comprises a dilator hub 102 that is coupled to an elongate member 120 that comprises regions of varying flexibility including an intermediate region 100*b* that terminates in a distal end region 100*a*. In accordance with an embodiment of the present invention, the intermediate region 100*b* is a substantially flexible or soft section that provides minimal resistance to deflection and is operable to be deflected under guidance to allow the dilator 100 to reach a desired site within a region of tissue within the patient's body to facilitate advancement of the distal end region 100*a* there-through. The flexible intermediate region 100*b* allows the dilator 100 to conform to the curvature of the steerable sheath 300 that is achieved through actuation of the steerable sheath 300. Thus, in some embodiments, as outlined herein, the flexible intermediate region 100*b* does not inhibit the range of motion of the steerable sheath 300.

Additionally, the elongate member 120 of the dilator 100 further comprises a distal end region 100*a* that is formed distally adjacent to the flexible intermediate region 100*b*, such that the flexible intermediate region 100*b* continues distally until (and terminates at) a proximal boundary or edge of the distal end region 100*a*. In other words the distal end region 100*a* extends proximally from the distal edge of the dilator 100 until a distal edge of the flexible intermediate region 100*b*. The distal end region 100*a* has a stiffness or rigidity that is greater than the flexible intermediate region 100*b* to facilitate advancement of the dilator 100 through the tissue once the dilator 100 has been positioned at the desired tissue site, such as a desired puncture site. The stiff or substantially rigid distal end region 100*a* provides enhanced pushability and may prevent deformation thereof during advancement of the distal end region 100*a* through the tissue (for example over a guide-wire or a puncturing device), for example at the puncture site in order to dilate the puncture site.

In one particular example, the elongate member 120 and the hub 102 may be formed, for example using techniques as may generally be known in the art, such as molding techniques. In some embodiments, the distal end region 100*a* is formed from a rigid polymer, and the intermediate region 100*b* is formed from a flexible polymer. In one particular embodiment, the rigid distal end region 100*a* is formed from High Density Polyethylene (HDPE) and the flexible or soft intermediate region 100*b* is formed from Low Density Polyethylene (LDPE). In some embodiments, the flexible intermediate region 100*b* may be formed from a material that exhibits sufficient flexibility to enable the flexible intermediate region 100*b* to conform to the curvature of a steerable sheath 300 and substantially does not impair, limit or inhibit the ability of the steerable sheath 300 to reach its intended curvature. Additionally, the rigid distal end region 100*a* is formed from a material that exhibits sufficient rigidity to enable the rigid distal end region 100*a* to be advanced through a tissue site such as through a puncture site within a region of tissue. Thus, dilator 100 can be understood to be a hybrid device in that it is sufficiently flexible to be guided to the tissue site yet maintains sufficient rigidity to be advanced through the tissue site.

As outlined previously, in accordance with an embodiment of the present invention, a dilator 100 is provided that is usable with a steerable sheath 300 to access a region of tissue within a patient's body. The steerable sheath 300 may be of the type shown in FIG. 1B comprising an articulating portion or deflectable region 200*b* that is amenable to deflection upon actuation of a steerable actuation mechanism for example such as a knob of a handle 302. During use, the dilator 100 is inserted within the steerable sheath 300 for use therewith such that a location or position of the flexible intermediate region 100*b* of the dilator 100 corresponds to the articulating portion or deflectable region 200*b* of the steerable sheath. This enables the steerable sheath 300 to reach its allowable range of curvatures or deflection (as shown and discussed later with reference to FIGS. 2A-2C), upon actuation, as minimal resistance is introduced by the dilator 100. In other words, the flexible intermediate region 100*b* of the dilator does not impart rigidity to the steerable sheath 300 as the dilator 100 is being steered by the steerable sheath 300. This enables the steerable sheath 300 to position the distal end region 100*a* of the dilator 100 at a desired target location within a region of tissue such as at a desired puncture location or site to enable the distal end region 100*a* to subsequently advance there-through for example to dilate the puncture site.

Figure 1C:
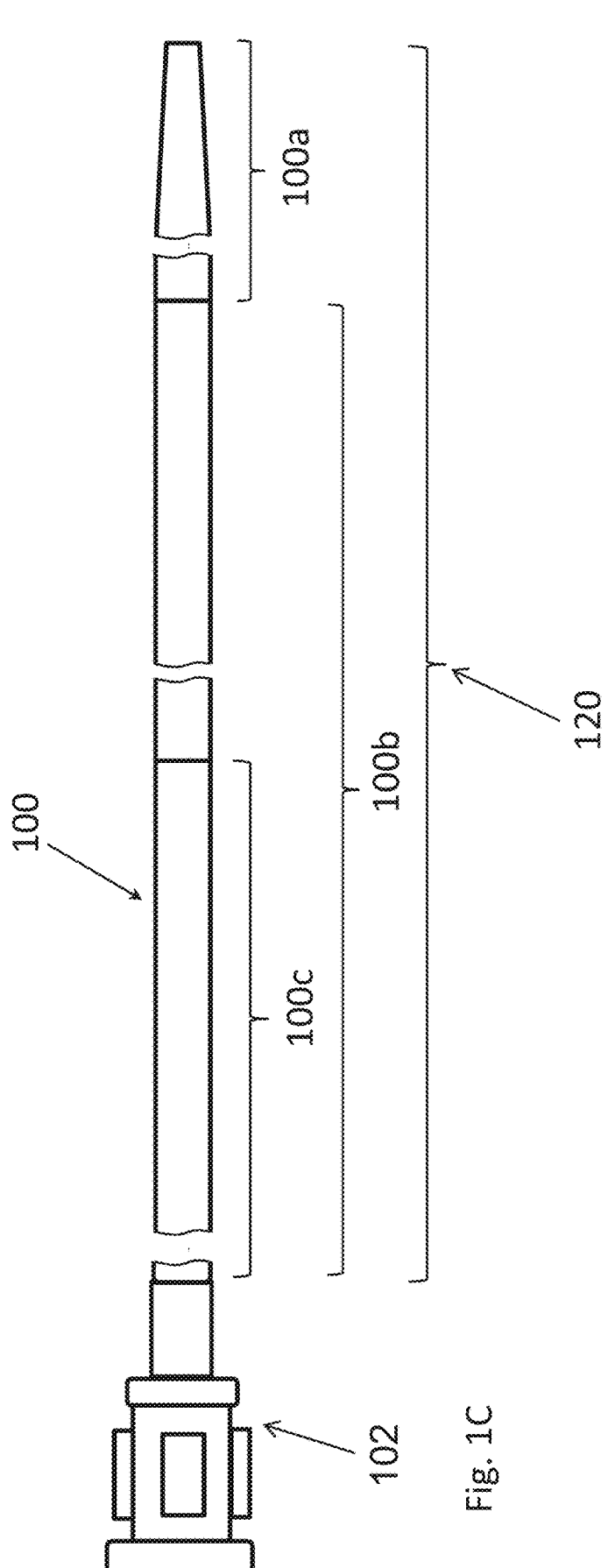
FIG. 1C is an illustration of a dilator in accordance with an alternate embodiment of the present invention.
Figure 1D:
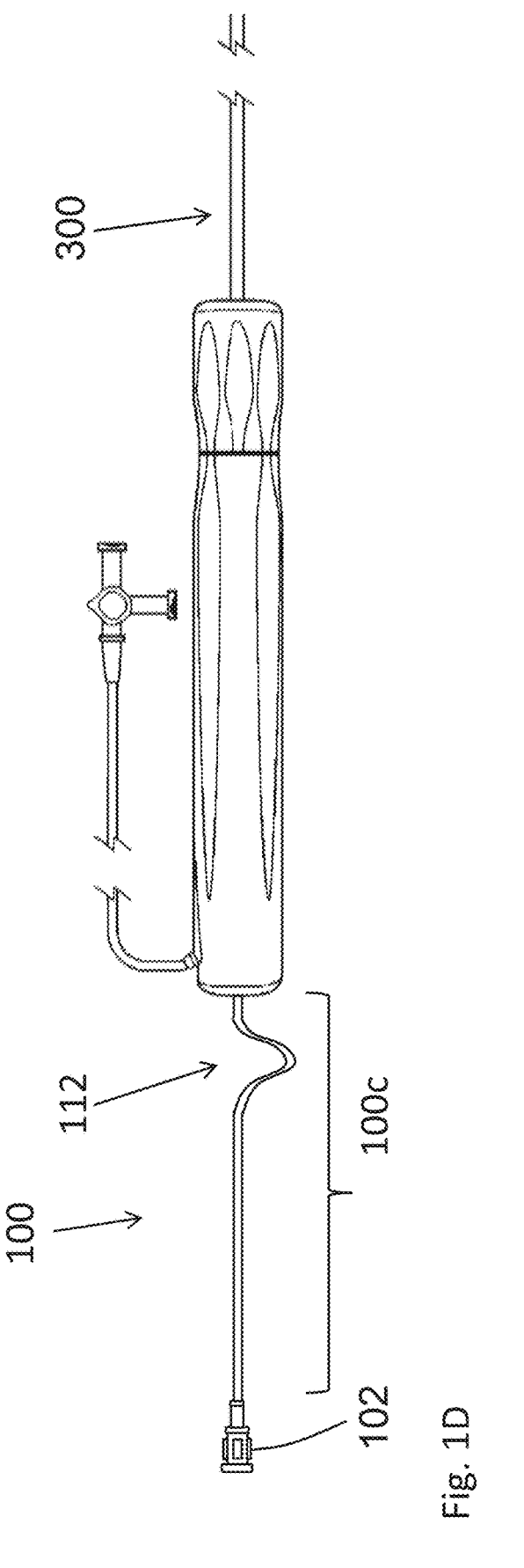
FIGS. 1D-1E illustrate a dilator within a steerable sheath in accordance with various embodiments of the present invention.

In one particular embodiment, with reference to FIG. 1A, dilator 100 further comprises a proximal region 100*c* that forms a part of elongate member 120 of dilator 100. The proximal region 100*c* extends proximally from the flexible intermediate region 100*b*. More specifically, the proximal region 100*c* extends proximally from a proximal boundary of the flexible intermediate region 100*b* and may extend until the hub 102. In some embodiments the proximal region 100*c* may also be formed from a flexible material and exhibits flexibility. Alternatively, in other embodiments, as shown in FIG. 1C, the flexible intermediate region 100*b* may extend along the proximal region 100*c* and may include the proximal region 100*c*. In some such embodiments, the flexible intermediate region 100b may have varying regions of flexibility. In some examples, a proximal region 100c is provided that is flexible as this may be desirable in certain applications. In some examples, flexibility of the dilator 100 in the proximal region 100c may lead to buckling observed in segment 112 of the proximal region 100c of the dilator 100 as the dilator is inserted into the steerable sheath 300, as shown in FIG. 1D. In some such embodiments, it may be desirable to provide stiffness or rigidity to the device proximal region 100c in order to make the dilator 100 less susceptible to buckling.

Figure 1E:
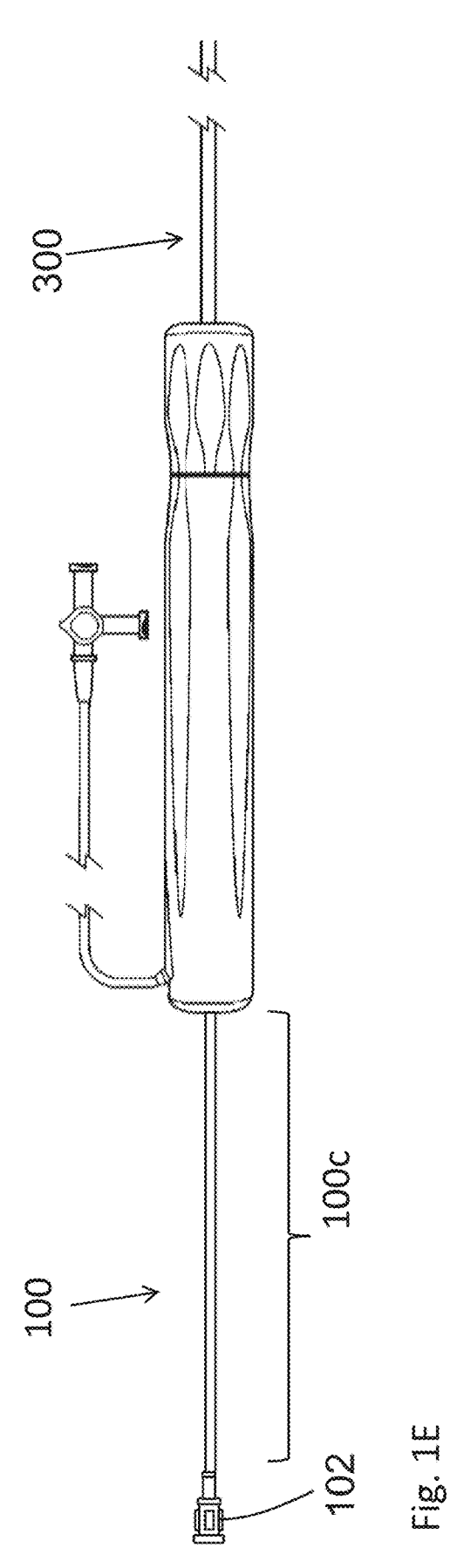

Therefore, in some embodiments as shown in FIG. 1E, a dilator 100 is provided where the proximal region 100c has a rigidity that is greater than that of the flexible intermediate region 100b. In some embodiments, the rigid proximal region 100c is formed from a material that exhibits sufficient rigidity to enable the rigid proximal 100c to be advanced through the steerable sheath 300 substantially without buckling or deforming. The rigidity of the dilator 100 in the proximal region 100c reduces the likelihood of the dilator bending or deforming as it is being inserted into the steerable sheath 300 during a procedure. In some embodiments, the distal end region 100a and the proximal region 100c have substantially the same rigidity. In a particular embodiment, the rigid distal end region 100a and the proximal region 100c are formed from a rigid polymer and the flexible intermediate region is formed from a flexible polymer. In one example, the rigid distal end region 100a and the proximal region 100c comprise substantially the same stiffness. In other embodiments, the rigidity of the rigid distal end region 100a and the proximal region 100c may differ. In one particular embodiment, the rigid distal end region 100a and the proximal region 100c are formed from High Density Polyethylene (HDPE) having a stiffness that is equal to about 0.8 GPa, whereas, the flexible intermediate region 100b is formed from Low Density Polyethylene (LDPE) having a stiffness of about 0.3 GPa. In other embodiments, the flexible and rigid regions of the dilator maybe formed from PEBAX® with different durometers of PEBAX® being used for the respective flexible and rigid regions.

In some embodiments, the dilator 100 has a usable length (i.e. the length of the elongate member 120) that is between about 60 cm to about 100 cm. More specifically, in one example, the dilator has a usable length of between about 67 cm and 68 cm. In a specific example of this, the dilator has a usable length of about 67.6 cm. In another example, the dilator has a usable length of between about 70 cm to about 71 cm. In a specific example of this, the dilator has a usable length of about 70.6 cm.

In some such embodiments, the flexible intermediate region 100b has a length of between about 7 cm to about 15 cm. In one particular example, the flexible intermediate region has a length of about 15 cm.

In some embodiments, the distal end region 100a has a length of between about 0.4 cm to about 4.0 cm. In a specific embodiment, the distal end region 100a has a length of about 0.5 cm to about 1 cm. In a particular example of this, the distal end region 100a has a length of between about 0.6 cm to about 0.7 cm. In a specific example, the distal end region has a length equal to about 0.7 cm. In some embodiments, the rigid distal end region 100a has a length of between about 2.5% to about 60% of the length of the flexible intermediate region.

In some embodiments, the rigid proximal section 100c may have a length of between about 41 cm to about 92 cm. In one particular embodiment, the proximal end section 100c has a length of about 51 to about 52 cm. In a specific example of this, the proximal end section has a length of about 51.9 cm.

Figures 2A, 2B:
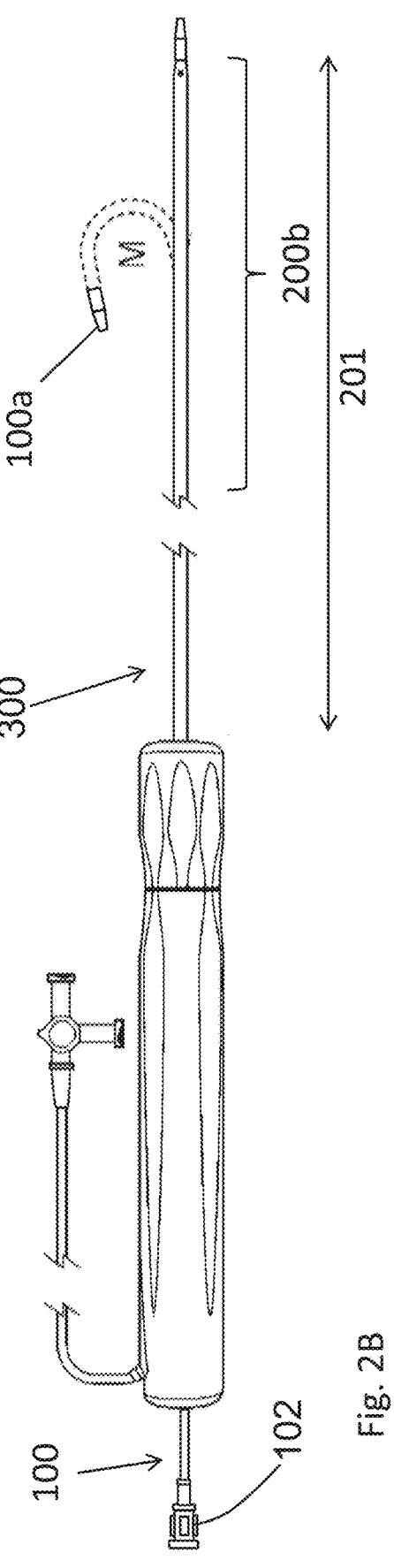
FIGS. 2A-2C illustrate a dilator in use with a steerable sheath, in accordance with various embodiments of the present invention.
Figure 2C:
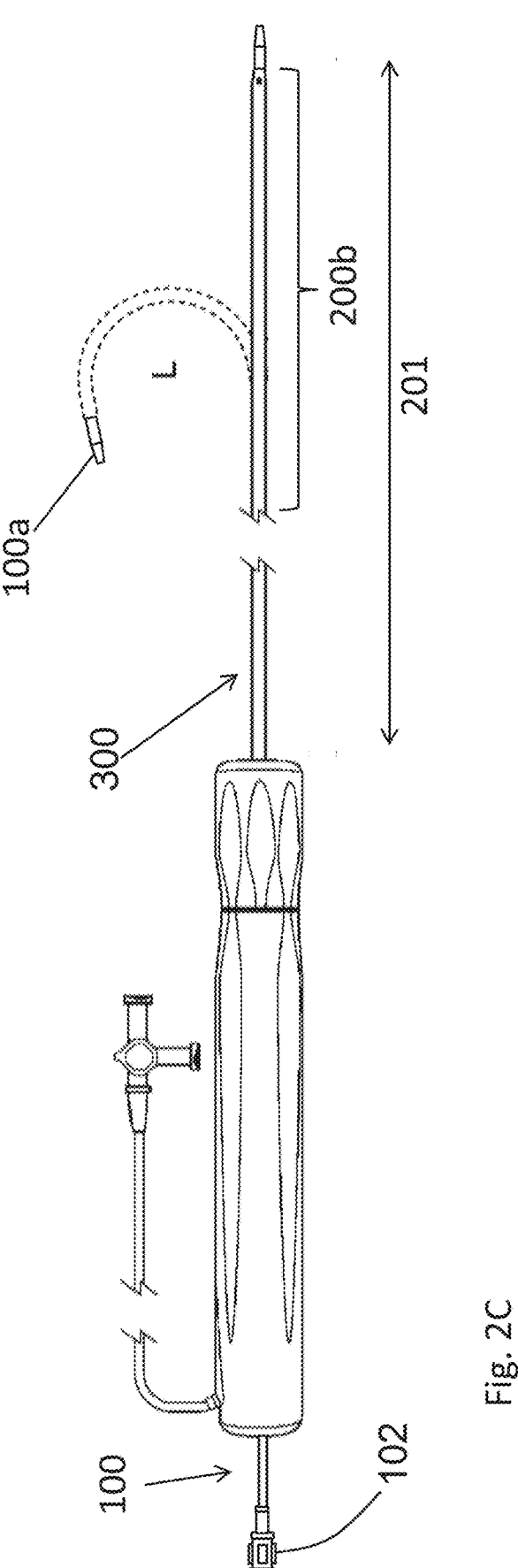

With reference now to FIGS. 2A-2C, various embodiments of a steerable sheath 300 are shown with the dilator 100 inserted there-through. In some embodiments, once the dilator 100 has been inserted through the steerable sheath 300, the dilator 100 extends by a distance, for example about 3 cm, distally beyond the distal end or tip of the steerable sheath 300 (more specifically, beyond the distal end/edge of the steerable sheath 300). In some embodiments, the dilator extends by between about 2 cm to about 4 cm beyond the distal edge of the steerable sheath 300. In some embodiments, the steerable sheath 300 has a usable length 201 that is between about 45 cm to about 71 cm.

In one specific example, with reference now to FIG. 2A, the steerable sheath 300 is an 8.5 French unidirectional steerable sheath, that has a deflectable region or articulating portion 200b operable to adopt a curve S having an angle of about 180 degrees and a having a radius of curvature of about 8.5 mm. Alternatively, in the example as shown in FIG. 2B, the deflectable region or articulating portion 200b of the steerable sheath 300 is operable to adopt a curve M having a radius of curvature of about 11 mm. In another example as shown in FIG. 2C, the deflectable region or articulating portion 200b of the steerable sheath 300 is operable to adopt a curve L, having a radius of curvature equal to about 25 mm.

With reference again to FIGS. 2A to 2C, in some embodiments, the usable length 201 of the steerable sheath 300 is equal to about 45 cm. In some such embodiments, the steerable sheath 300 is used with an 8.5 French flexible dilator 100 having a usable length of about 67 cm and comprising a flexible intermediate region 100b with a length of about 15 cm. Thus, in accordance with various embodiments of the present invention, a steerable sheath 300 and dilator 100 are provided that work in conjunction with each other, with the steerable sheath 300 and dilator 100 having suitable lengths and sizes (including inner and outer diameters) that are usable to reach a desired region of tissue when inserted through the vasculature.

With reference now to FIGS. 3A-3D, various dilator distal tip configurations are shown with alternative distal end regions 100a. In the particular example shown in FIG. 3A, the dilator 100 comprises a taper 122 along a distal end of the dilator 100, forming a tapered distal tip 106. In the example shown, the distal end region 100a extends partially along the length of the taper 122 and as such forms a part of the taper 122. In a specific example of this, the taper 122 has a length of about 1 cm. In one such example the rigid distal end region 100a has a length of about 0.7 cm. In another such example, the rigid distal end region 100a has a length of between about 0.3 cm to about 0.5 cm.

Figure 3A:
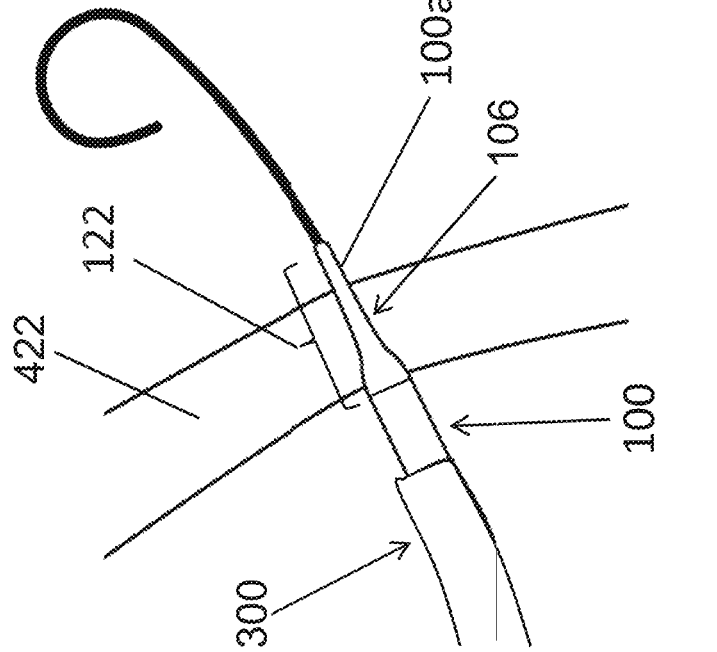
FIGS. 3A-3E illustrate various distal tip configurations of a dilator in accordance with an embodiment of the present invention.
Figure 3B:
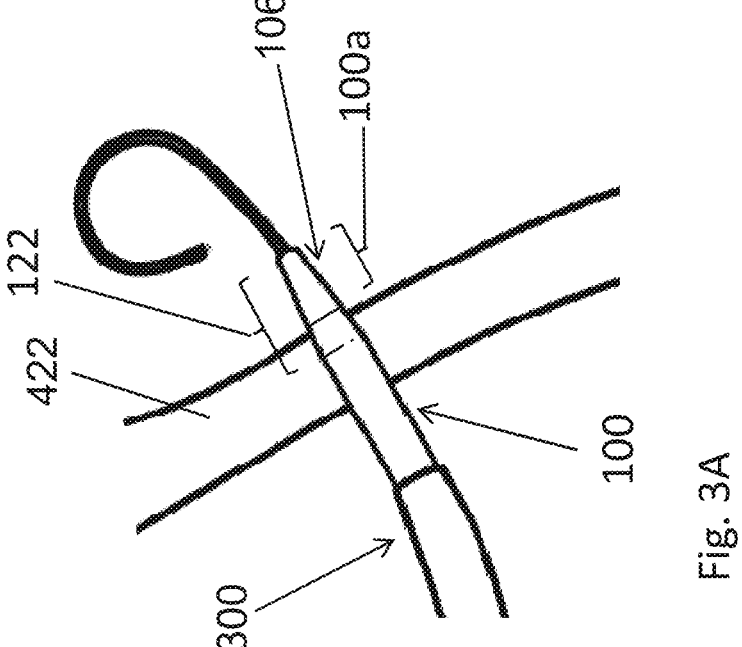
Figure 3D:
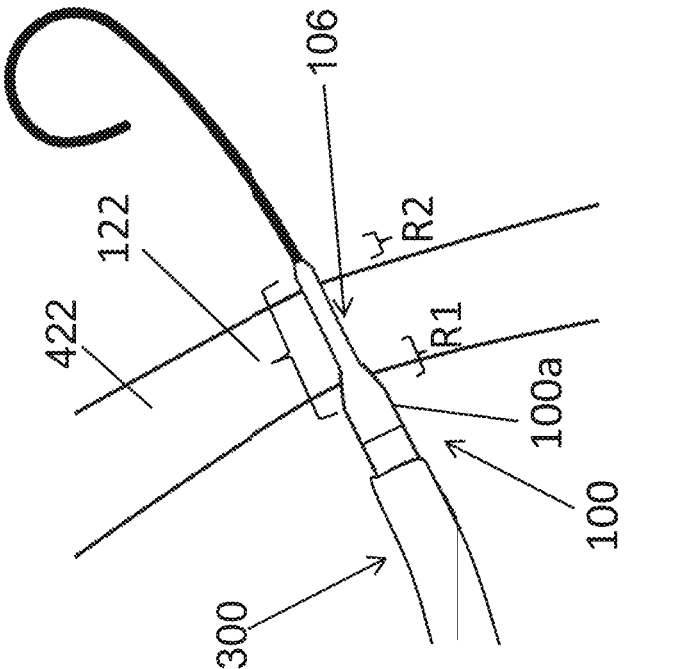
Figure 3C:
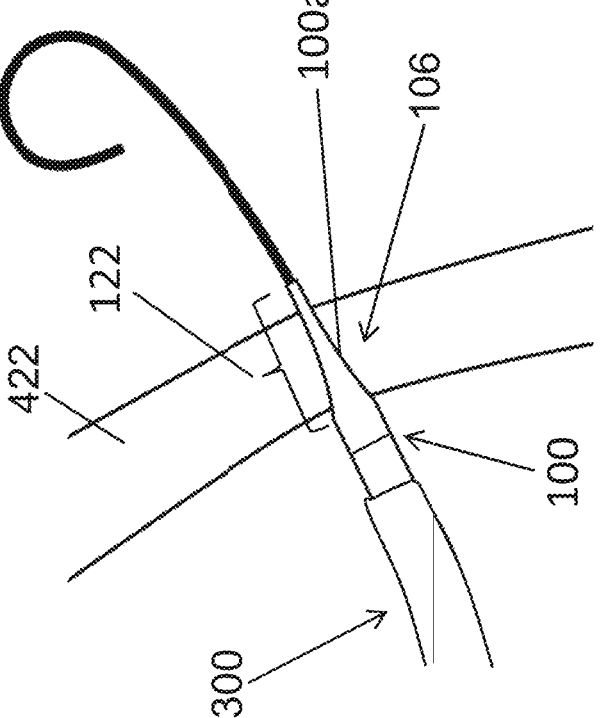

FIGS. 3B, 3C and 3D illustrate alternative configurations for the tapered distal tip 106. As shown in FIG. 3B, in some embodiments, the distal end region 100a may extend along the entire length of the taper 122. In a further example of this, as shown in FIGS. 3C and 3D, the distal end region 100a may additionally extend further proximally along the elongate member 120, beyond the taper 122.

FIG. 3C illustrates a dilator 100 that is an 8.5 French dilator that tapers down to an outer diameter (OD) of about 0.046" (about 1.2 mm) and an inner diameter (ID) of about 0.036" (about 0.9 mm), along the tapered distal tip 106. In a specific example, the taper 122 has a length of about 2 cm. In some such embodiments, the distal end region 100a has a length of about 3 cm and is formed from HDPE, whereas the flexible intermediate region is formed from LDPE. The dilator 100 may be formed from a re-flow of the two polymers, HDPE and LDPE, in a glass die via lap joining.

Additionally, FIG. 3D illustrates a dilator 100 that has a distal tip 106 that comprises a double taper configuration. In one specific example, the dilator 100 is an 8.5 French dilator that tapers down to about 5.6 French along a first tapered region R1, with the first tapered region R1 having a length of about 1 cm. The dilator 100 then tapers from about 5.6 French to an outer diameter (OD) of about 0.046" and an inner diameter (ID) of about 0.036", along a second tapered region R2, with the second tapered region have a length of about 1 cm. In one specific example, the distance between the first and second tapered regions R1 and R2 is also equal to about 1 cm. In one such example, the distal end region has a length of about 4 cm. The dual taper configuration may provide greater feedback during dilation and may allow the user to feel the tactile feedback (in the form of a pop) associated with each of the first and second tapered regions R1 and R2. The dual taper configuration may be formed in a similar manner to above, using a glass tipping die via lap joining.

In some embodiments, the dual taper distal tip configuration shown in FIG. 3D may require less force to advance it through a tissue site (for example, through a puncture within a region of tissue) than a single taper distal tip configuration, as shown FIGS. 3B and 3C. Furthermore, in some examples, a longer taper length (as shown and discussed with respect to FIG. 3C) may require less force to be advanced through tissue than a shorter taper length (as shown in FIG. 3A). The longer taper provides a lower slope and hence a smoother transition. Additionally, the longer taper length may prevent high mechanical resistance when the dilator is advanced through a puncture site and may prevent the dilator from slipping away from the puncture site. Additionally, in examples where the dilator is used to dilate a puncture within a septum of the heart (where access is provided through the right atrium and an RF wire is used to create the puncture as described further below), the longer taper length may prevent the RF wire from being pulled back into the right atrium of the heart and losing the puncture site and thus may help prevent the need to create a second puncture.

Furthermore, in some embodiments, the dilator 100 comprises a straight dilator that substantially lacks a curvature. In other words, the dilator 100 has a substantially straight configuration along each of the rigid proximal region 100c, the flexible intermediate flexible portion 100b and the rigid distal end region 100a. During use, the straight dilator 100 does not impart a curvature to the steerable sheath 300 to enable the steerable sheath 300 to reach its desired curvature upon actuation. This allows the steerable sheath 300 to position the distal end region 100a at a desired target location, for example at a desired puncture site to enable the distal end region 100a to advance there-through to dilate a puncture once it has been formed. Therefore, the straight dilator 100 does not interfere with or affect the intended curvature of the steerable sheath 300 and thus does not inhibit the desired range of motion of the steerable sheath 300. In accordance with an embodiment of the present invention, the dilator 100 comprises both a straight configuration and a flexible or soft intermediate region 100b, and the combination provides a synergistic or combined effect preventing the dilator 100 from inhibiting the range of movement of the articulating portion or deflectable region 200b of the steerable sheath 300. This may allow the steerable sheath 300 to guide the dilator 100 to access a region of tissue within a patient's body such as for example an area of the heart.

Figure 3E:
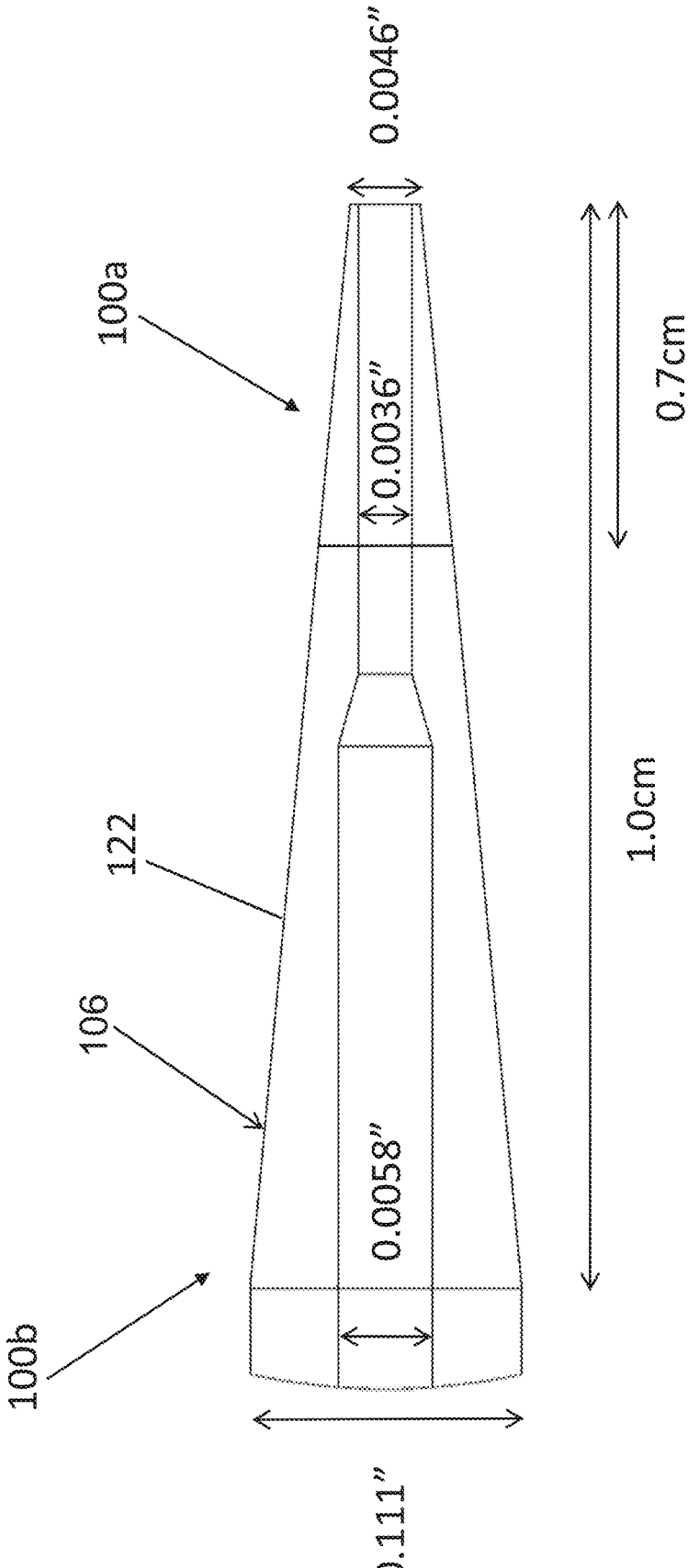

In a specific example, as shown in FIG. 3E, a dilator 100 is provided that is an 8.5 French dilator. Along the proximal region 100c and flexible intermediate region 100b (not including the taper 122), the dilator has an outer diameter (OD) that is equal to about 0.111"+/−0.002" and an inner diameter (ID) that is equal to about 0.058"+/−0.002", that tapers down along the tapered distal tip 106 to an outer diameter of about 0.044"+/−0.001" and an inner diameter of about 0.036"+/−0.001" at the distal boundary or edge of the distal tip 106. This allows the dilator 100 to be compatible with a 0.035" OD guide-wire. Furthermore, the taper 122 along the tapered distal tip 106 has a length of about 1 cm and the rigid distal end region 100a has a length of about 0.7 cm. In one such example, the dilator 100 has a usable length of about 67.6 cm, with the flexible intermediate region 100b having a length of about 15 cm, with the rigid proximal region 100c having a length of about 51.9 cm. In one particular embodiment, the rigid distal end region 100a and the proximal region 100c are formed from High Density Polyethylene (HDPE) having a stiffness of 0.8 GPa, whereas, the flexible intermediate region 100b is formed from Low Density Polyethylene (LDPE) having a stiffness of about 0.3 GPa. In the example described herein, the dilator 100 comprises varying regions of flexibility (i.e. flexible and rigid regions), and since the dilator 100 comprises a fairly constant OD and ID, the behavior or various regions, in terms of rigidity, is governed by the stiffness of the materials used.

In embodiments described herein, the flexural rigidity value of the dilator 100 is the product of Young's modulus E (in Pa) [also known as the flexural modulus) which indicates stiffness of a material, and the second moment of area (or area moment of inertia I) (in $m^4$), having SI units of $Pa \cdot m^4$ which also equals $N \cdot m^2$. The area moment of inertia I may be calculated from the values of the inner diameter (ID) and the outer diameter (OD) by a person skilled in the art using the formula $[I=\pi/64(OD^4-ID^4)]$. In one particular example discussed herein, the flexural rigidity value is calculated to be 0.0023 $N \cdot m^2$ for the flexible intermediate region 100b comprising LDPE and 0.00086 $N \cdot m^2$ for the rigid proximal region 100c comprising HDPE. In some embodiments, the ID of the dilator 100 along the flexible intermediate region 100b and the rigid distal end 100a (not including the taper), ranges from between about 0.056" to about 0.06". In some such embodiments, the OD of the dilator 100 along the flexible intermediate region 100b and the rigid distal end 100a (not including the taper), ranges from between about 0.109" to about 0.113". In some embodiments, the flexible intermediate region 100b comprising LDPE, has a rigidity that ranges from between about 0.00030 $N \cdot m^2$ to about 0.0014 $N \cdot m^2$, and the rigid distal end region 100a comprising HDPE has a rigidity that ranges from between about 0.0015 $N \cdot m^2$ to about 0.0046 $N \cdot m^2$.

Figure 4:
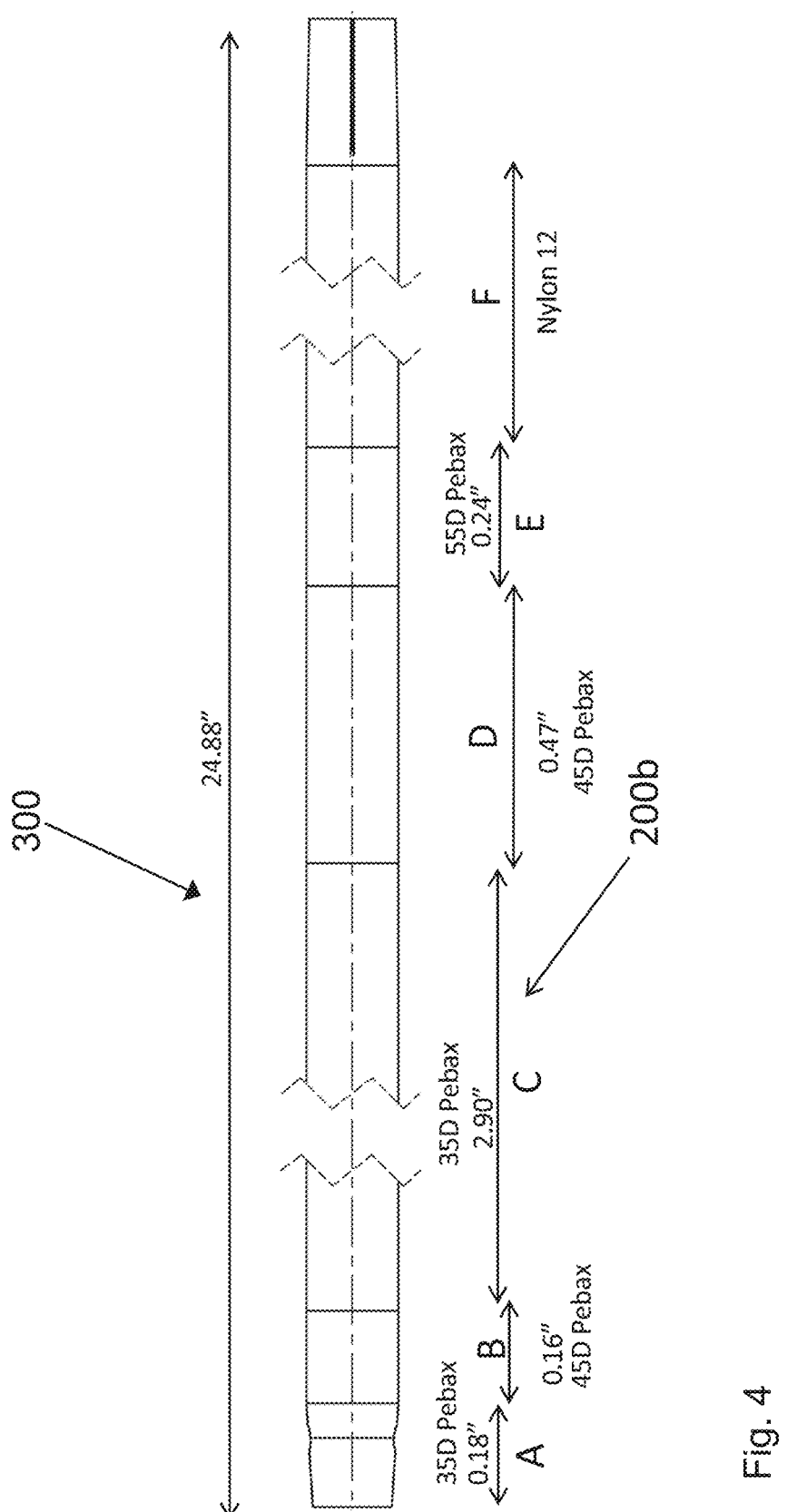
FIG. 4 illustrates an embodiment of a steerable sheath suitable for use with an embodiment of a dilator of the present invention.

In one particular example, the dilator 100 is usable with a steerable sheath 300 that is an 8.5 French unidirectional steerable sheath, as shown in FIG. 2A, that has a deflectable region or articulating portion 200b that is operable to deflect with a curve S having an angle of about 180 degrees and with a radius of curvature of about 8.5 mm. The steerable sheath 300 has a length equal to about 45 cm. In one particular example, the steerable sheath 300 may be a SUREFLEX™ Steerable Sheath sold by Baylis Medical Company Inc., as shown in FIG. 4. The steerable sheath 300 comprises a metal wire braid comprising a High Tensile 304v Stainless Steel 0.002"×0.006" with a polymer jacket disposed thereon, and an inner PTFE liner. The polymer jacket comprises sections of PEBAX and Nylon with varying durometers (D) and lengths. The deflectable portion of the steerable sheath 300 is indicated by reference number 200b.

In one such embodiment, a steerable sheath assembly is described with the dilator 100 being inserted within the steerable sheath 300. In a particular example of this, the steerable sheath 300 is actuated to reach an angle of about 90 degrees. In one such example, the actual observed deflection of the steerable sheath 300 is equal to about 80 degrees. Thus, the steerable sheath 300 is able to reach about 88.8% of its intended curvature. As such the dilator 100 allows the steerable sheath 300 to substantially reach its intended curvature. Conversely, unlike the embodiments of the present invention, when a rigid HDPE dilator with similar dimensions is used (i.e. a dilator with similar ID and OD that comprises entirely of HDPE) the steerable sheath 300 is only able to reach a 45 degree curvature which is about half of the intended curvature.

In an additional example, the steerable sheath 300 is actuated to reach a deflection angle of about 180 degrees, however, an actual deflection equal to about 140 degrees is observed. Thus, the steerable sheath 300 is able to reach 77.8% of its intended curvature. Contrary to this, when the steerable sheath 300 is used with a rigid HDPE dilator, the steerable sheath 300 is only able to reach a 90 degree curvature.

In still an additional example, the steerable sheath 300 is actuated to reach a deflection angle of about 250 degrees with the actual observed deflection being equal to about 180 degrees. Thus, the steerable sheath is able to reach about 72% of its intended curvature. On the other hand, when the steerable sheath 300 is used with a rigid HDPE dilator, the steerable sheath 300 is only able to reach a curvature of about 110 degrees.

As such, in the examples outlined above, the flexible intermediate region 100b of dilator 100, in accordance with an embodiment of the present invention, substantially does not inhibit the range of motion of the steerable sheath 300, allowing the steerable sheath 300 to reach its intended shape or curvature in order to access a desired tissue site within a region of tissue within a patient's body. Thus, in some embodiments the dilator 100 allows the steerable sheath to reach a curvature that is equal to at least about 70% of its intended curvature. In other embodiments the dilator 100 allows the steerable sheath to reach a curvature that is equal to greater than about 50% of the intended curvature.

In one particular embodiment, the dilator 100 is usable with an ancillary device such that it allows the ancillary device to maintain or reach its intended shape or curvature in order to access a desired tissue site within a region of tissue within a patient's body. The dilator 100 may be of the type described herein above, that comprises a rigid distal end region 100a and a flexible intermediate region 100b terminating at the distal end region 100a, with the rigid distal end region 100a having a rigidity greater than the flexible intermediate region 100b to enable the dilator 100 to advance through tissue. The dilator 100 is configured for use in conjunction with the ancillary device such that during use, the flexible intermediate region 100b corresponds to a region of the ancillary device that is functional for imparting or providing a curvature. In one particular example, the dilator 100 is advanced over or through the ancillary device such that such that during use the flexible intermediate region 100b of the dilator 100 does not affect the region of the ancillary device that is functional for imparting a curvature, allowing the ancillary device to substantially maintain or reach its intended position or shape in order to position the dilator rigid distal end region 100a at a desired location within the region of tissue.

In one such example, the ancillary device comprises a steerable device such as a sheath, catheter or guide-wire that is steerable, where the ancillary device is functional for imparting a curvature by actuation of the ancillary device. When in use in conjunction with the dilator 100, the flexible intermediate region 100b of the dilator does not inhibit or prevent the ancillary device from reaching its intended curvature upon actuation to position the dilator distal end region 100a at a desired location.

Alternatively in some embodiments, the ancillary device comprises a fixed curve device such as a fixed curve sheath that has a preformed curve. Similar to embodiments discussed previously herein, the fixed curve sheath is usable with the dilator 100 and during use the flexible intermediate region 100b of the dilator 100 does not affect the preformed curvature of the sheath, thus allowing the sheath to position the rigid distal end 100a of the dilator 100 at the desired location within the region of tissue. Furthermore, the use of the dilator 100, in accordance with an embodiment of the present invention, may prevent the need for over curving the sheath in anticipation of a substantial decrease in curvature of the sheath once the dilator 100 there-through.

In one such example, a fixed curve sheath is described with the dilator 100 being inserted therein. The fixed curve sheath has a pre-formed curve with an angle of about 40 degrees. Once the dilator 100 is positioned through the fixed curve sheath, the curvature of the sheath is observed to be about 32 degrees. Thus, the fixed curve sheath is able to maintain its curvature at about 80% of the intended curvature. As such the dilator 100 allows the fixed curve sheath to substantially maintain its intended curvature. Contrary to this, if a rigid HDPE dilator is utilized, unlike embodiments of the present invention (as described previously herein above), the curvature of the fixed curve sheath is reduced to about 22.5 degrees.

Similarly in another example, a fixed curve sheath is described that has a pre-formed curvature with an angle of about 135 degrees. Once a dilator 100, is inserted through the sheath in accordance with an embodiment of the present invention, the observed angle of curvature of the fixed curve sheath, is equal to about 112 degrees. Thus, the fixed curve sheath 300 is able to maintain a curvature that is equal to about 77.8% of its intended curvature. Contrary to this, if a rigid HDPE dilator is utilized, unlike embodiments of the present invention, the curvature of the fixed curve sheath is reduced to about 78 degrees. Thus, in some such embodiments, the fixed curve sheath is able to maintain an angle of curvature that is greater than about 60% of its intended curvature. In other embodiments, the fixed curve sheath is able to maintain an angle of curvature that is equal to at least about 75% of its intended curvature.

As outlined above, in some embodiments described herein above, the dilator 100 comprises varying regions of flexibility (i.e. rigid and flexible regions) to define a hybrid medical device. Since the dilator 100 comprises a fairly constant OD and ID and thus fairly constant wall thickness along its length, the behavior of the various regions, in terms of rigidity, is governed by the stiffness of the materials used. For example, the higher the stiffness of a material, the greater the rigidity, and the lower the stiffness of the material the lower the rigidity. Alternatively, in other embodiments, a single material may be used to form the dilator where the varying regions of flexibility are provided by varying the wall thickness along the respective regions. For example, an HDPE dilator may be provided with a relatively thin wall thickness along the flexible intermediate region and a relatively thicker wall thickness along the distal end region, in order to provide a dilator with the functionality described previously hereinabove.

Puncture Devices

In accordance with further embodiments of the present invention, as described hereinabove, FIGS. 5A-5F illustrate embodiments of a medical device operable to be guided to a tissue site to puncture tissue and to function as a rail for installing devices thereupon. Such embodiments provide efficiencies to medical procedures in which they are utilized as they perform multiple functions and thereby reduce the amount of device exchanges that need to be performed. The "hybrid" medical devices described herein further facilitate the access and puncture of a tissue site upon insertion at a particular access site on a patient's body, as described hereinabove.

Figure 5A:
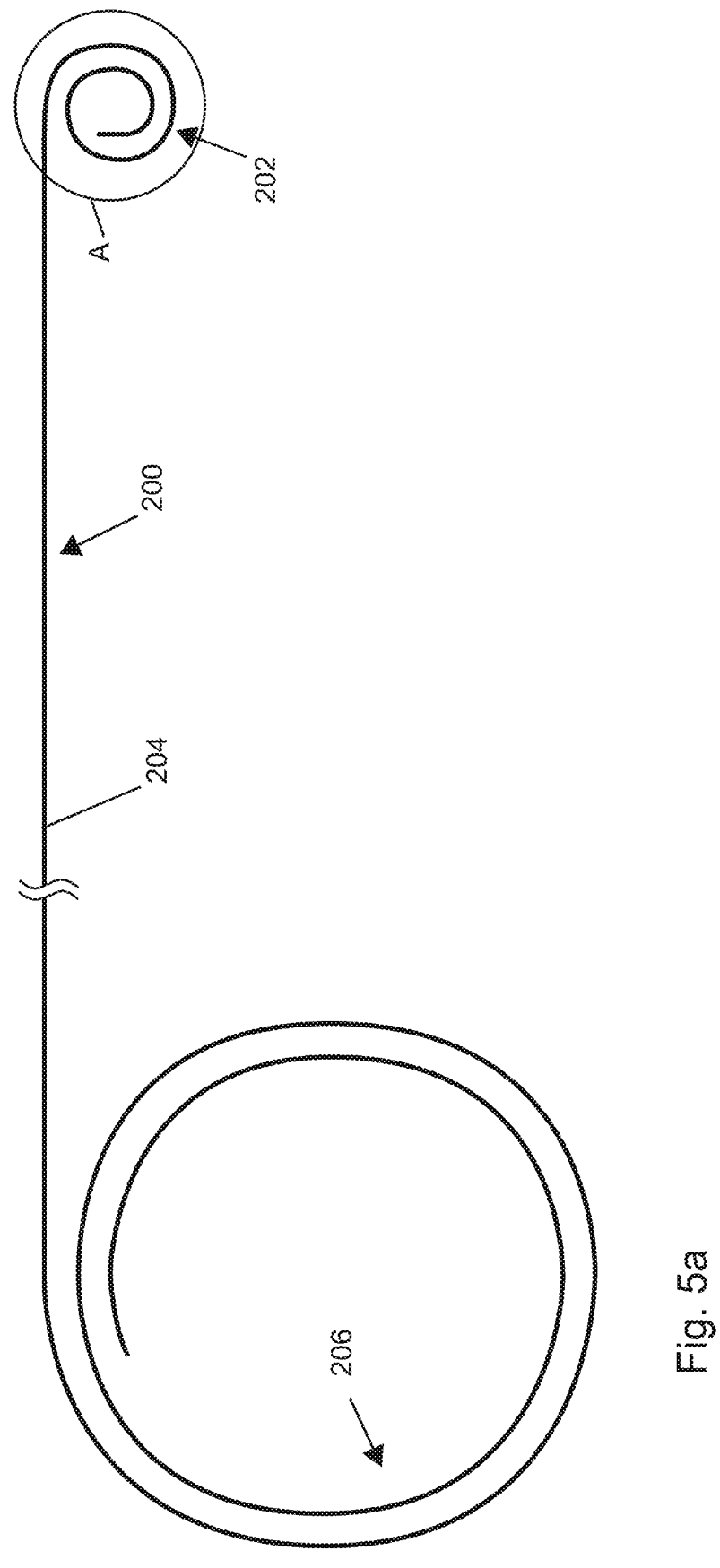
FIG. 5A is a side view of an embodiment of a medical device, for example a multi-function guidewire of the present invention.

With reference to FIG. 5A, an embodiment of a medical device, referred to herein as multi-function guidewire 200, is shown. Multi-function guidewire 200 includes an elongate member which comprises a proximal section 206 which is typically curved, a rail section 204, and a distal section 202 which is also typically curved. Multi-function guidewire 200 is sufficiently flexible to enable access to heart tissue, such as a septum, from, for example, an inferior approach or a superior approach. Thus, multi-function guidewire 200 allows access to a particular tissue site from one of several vascular access sites. While certain aspects and features of the multi-function guidewire 200 will be presently described with reference to one specific application, namely creating a puncture in a heart septum, it will be understood by those of skill in the art that the medical device described herein is usable in various applications and its utility is not limited to this particular procedure.

An active tip 208 (shown in detail in FIG. 5E) at the distal end of the distal section 202 is operable to deliver energy for puncturing tissue such as a heart septum to create a puncture site through which distal section 202 and the distal part of rail section 204 can be advanced, for example to enter the left atrium. Once advanced through the puncture site, distal section 202 is biased to form a coil for anchoring multi-function guidewire 200 beyond the puncture site. Typically, when distal section 202 is advanced out of a dilator and beyond the septum to curl up into a coil in the left atrium, the distal end of the rail section will have been advanced into the left atrium i.e. in order for the distal section to form a coil, rail section 204 is typically advanced into the left atrium to define a rail thereto. In some embodiments, particularly for use in accessing the left atrium, the distal section 202 is sized such that when it forms a coil in the left atrium, the coil will not be accidentally advanced into openings adjacent the left atrium, such as a left pulmonary vein or a mitral valve. Once the guidewire is anchored, rail section 204 functions as a substantially stiff rail for supporting the installation of one or more tubular members thereupon and for advancing devices into the heart. In typical embodiments, rail section 204 includes a metal wire 212 (FIG. 5B) which is fabricated of spring tempered steel. In some embodiments, for example when accessing the heart from a superior approach, the rail is sufficiently flexible to bend about 180° and yet maintains sufficient rigidity to function as a rail for advancing devices thereover. Additionally, the flexibility of rail section 204 enables it to be maneuvered (for example, by a steerable sheath) to access a tissue site. Thus, as described with respect to dilator 100 above, a medical device such as multi-function guidewire 200 can be understood to be a "hybrid" device, having sufficient flexibility to be positioned at a tissue site from a particular access site, while being sufficiently rigid to function as a rail for installation of other devices thereupon.

Figure 5B:
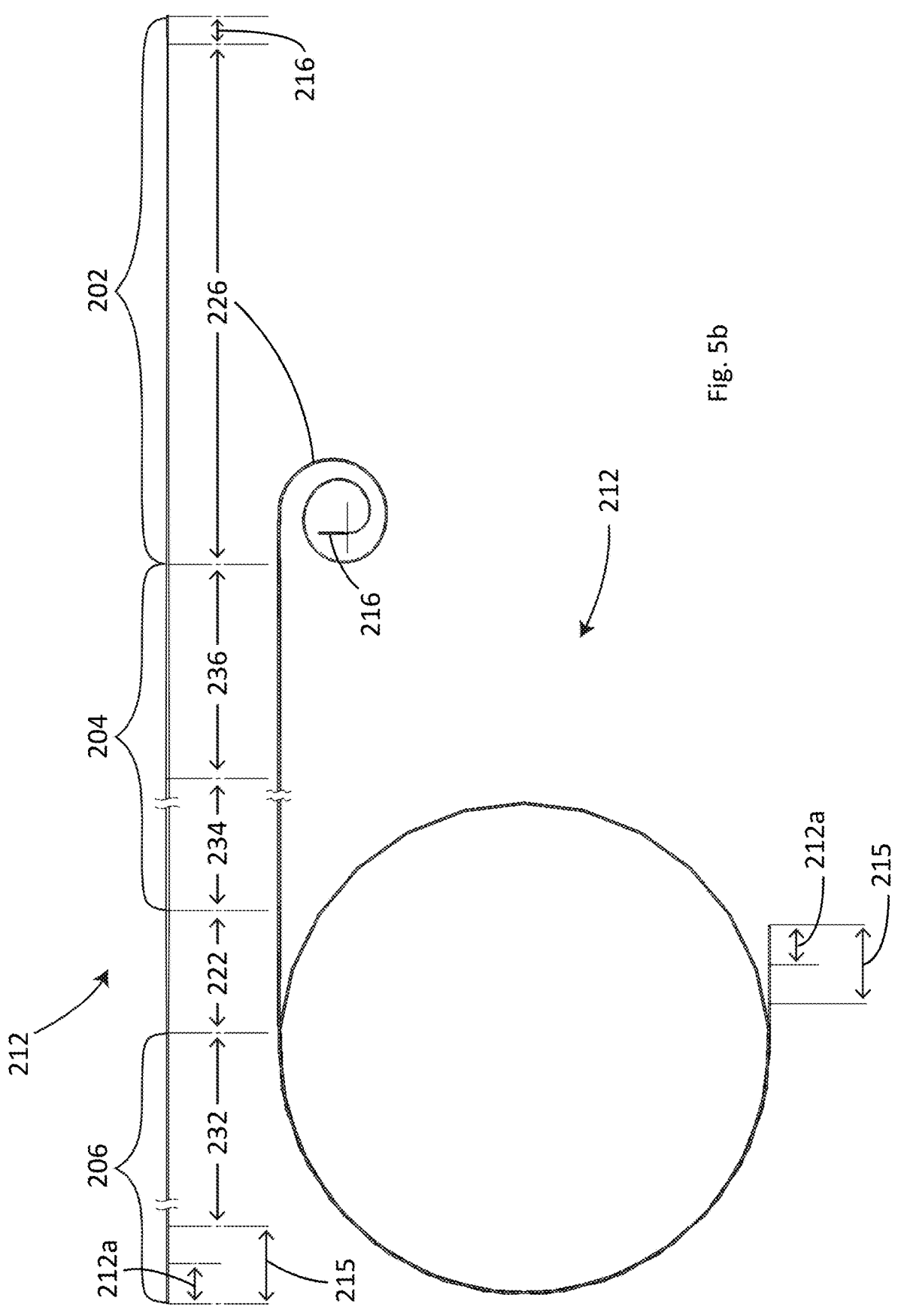
FIG. 5B includes side views of an internal metal wire of a multi-function guidewire in a straight configuration and a corresponding coiled configuration.

In some embodiments of the multi-function guidewire 200, rail section 204 has a length of about 700 mm to about 1750 mm to enable access to the tissue site. In some embodiments, the rail section has a length of between about 1200 and 1300 mm, more particularly about 1240 mm. Typically, as shown in FIG. 5B, the rail section has a constant diameter in maximum rail portion 234 and tapers distally in tapered rail portion 236. In some examples, the rail section (including metal wire 12 and insulation 214, described further hereinbelow) has an outer diameter of about 0.86 mm (0.034 inches) at its proximal end (i.e. at maximum rail portion 234) and about 0.71 mm at its distal end (i.e. at the distal end of tapered rail portion 236). In some such embodiments, the diameter of the guidewire elongate member is constant throughout maximum rail portion 234. In some embodiments, the upper limit for the outer diameter of the proximal end of the rail section (including metal wire 12 and insulation 214) is about 1.1 mm and the lower limit of the outer diameter of the distal end of rail section 204 (distal end of tapered rail portion 236) is about 0.6 mm. In some alternative embodiments, the outer diameter tapers in maximum rail portion 234.

The proximal section 206 is biased to a coiled configuration for improved handing of the medical device, for example to avoid interfering with users of the device such as doctors, nurses and other medical personnel. In some embodiments, the proximal section is biased to assume a spiral-shaped coil, while in other embodiments; it is biased to assume a constant diameter coil (i.e. the diameter across the entire coil is substantially constant). In some embodiments, proximal section 206 has a length of about 150 to about 600 mm. In one specific example, proximal section has a length of about 500 mm.

For ease of illustration of the primary sections of multi-function guidewire 200, these sections are shown in FIG. 5B, as follows: the lower part of the figure shows the wire 212 of guidewire 200 in a typical configuration in use, with both distal section 202 and proximal section 206 adopting a coil shape, while the upper portion of the figure shows the wire 212 in a straight configuration. The divisions between the different sections of multi-function guide-wire 200 are shown by construction lines between the top and bottom drawings, with the exception of the two end parts, proximal section straight portion 215 and distal section straight portion 216.

Referring to the straight configuration wire shown in the upper part of FIG. 5B, proximal section 206 includes proximal section straight portion 215 and proximal section curved portion 232. Typically, wire 212 has a constant diameter in proximal section 206. Transition portion 222 is located between proximal section 206 and rail section 204. The diameter of wire 212 increases distally through transition portion 222. Referring to the coiled configuration of wire 212, shown in the lower part of FIG. 5B, proximal section straight portion 215 is shown at the bottom of the coil formed by proximal section 206. The proximal end of straight portion 215 includes an exposed portion 212a of electrically conductive wire 212.

Rail section 204 includes maximum (or 'constant-diameter') rail portion 234 and tapered rail portion 236. Typically, maximum rail portion 234 has a constant diameter along its length which generally corresponds to the largest diameter of the wire. In some embodiments, the diameter of wire 212 tapers distally through tapered rail portion 236.

Distal section 202 is distal of rail section 204 and includes distal section curved portion 226 and distal section straight portion 216. Distal section straight portion 216 is shown, in the lower portion of FIG. 5B, inside of the coil formed by distal section 202.

Typically, wire 212 is comprised of spring tempered stainless steel.

In some embodiments, wire 212 of the rail section has an outer diameter of about 0.64 mm (more specifically, 0.6 mm) at maximum rail portion 234 and at a proximal end of the tapered rail portion 236 (i.e. the diameter is constant in maximum rail portion 234); and an outer diameter of about 0.5 mm at a distal end of tapered rail portion 236 of the rail section 204. More broadly, embodiments of the wire 212 of the rail section have an outer diameter ranging from about 0.89 mm and to about 0.36 mm, or about 0.9 mm to about 0.3 mm, with the diameter of wire 212 typically being constant in maximum rail portion 234. In alternative embodiments, the outer diameter tapers in maximum rail portion 234.

In some embodiments, the proximal end of rail section 204 (i.e. the proximal end of maximum rail portion 234) of wire 212 has a stiffness of 2119 N/m or less. In some embodiments, the distal end of tapered rail portion 236 has a stiffness of 118 N/m or more. Typically, the stiffness is constant throughout the length of maximum rail 234, but it may decrease distally in alternative embodiments. In one example, the proximal end of rail section 204 (the proximal end of maximum rail portion 234) has a stiffness of about 550+/−5 N/m, more specifically 552 N/m, and the distal end of tapered rail 236 has a stiffness of about 200+/−5 N/m, more specifically 204 N/m, to enable the rail section to be bendable by at least 180 degrees and to function as a rail for supporting installation of one or more tubular members thereupon. In another embodiment, the rail section has a stiffness of between about 100 N/m to about 600 N/m. It should be noted that the stiffness values noted herein are derived using a 3-point bend test over a 50 mm span, as would be understood to those of skill in the art.

For ease of understanding, a table of correspondence is included for converting certain of the stiffness measurements included herein to normalized flexural rigidity:

| Wire diameter (mm) | Stiffness in three point bending over span of 50 mm (N/m) | Flexural rigidity (N*m^2) |
|---|---|---|
| 0.635 | 552 | 1.4E−3 |
| 0.5 | 204 | 5.3E−4 |
| 0.89 | 2119 | 5.5E−3 |
| 0.43 | 118 | 3.1E−4 |
| 0.157 | 2.1 | 5.4E−6 |
| 0.127 | 0.88 | 2.0E−6 |

The diameter of wire 212 (and thereby multi-function guide-wire 200) decreases distally along distal section curved portion 226 of the distal section, and alternately decreases and increases distally in distal section straight portion 216 (explained below, with reference to FIG. 5F).

In typical embodiments, a layer of electrical insulation 214 (FIG. 5D) covers electrically conductive wire 212, with the exception of active tip 208 at the distal end of multi-function guide-wire 200 and an electrically exposed portion

212a at the proximal end of the guidewire, both of which remain electrically exposed. Exposed portion 212a is part of proximal section straight portion 215 and is operable to be electrically connected to an electrosurgical generator. Proximal section straight portion 215 facilitates loading/installation of over-the-wire devices (e.g. tubular members) onto the multi-function guidewire.

Figures 5C, 5D:
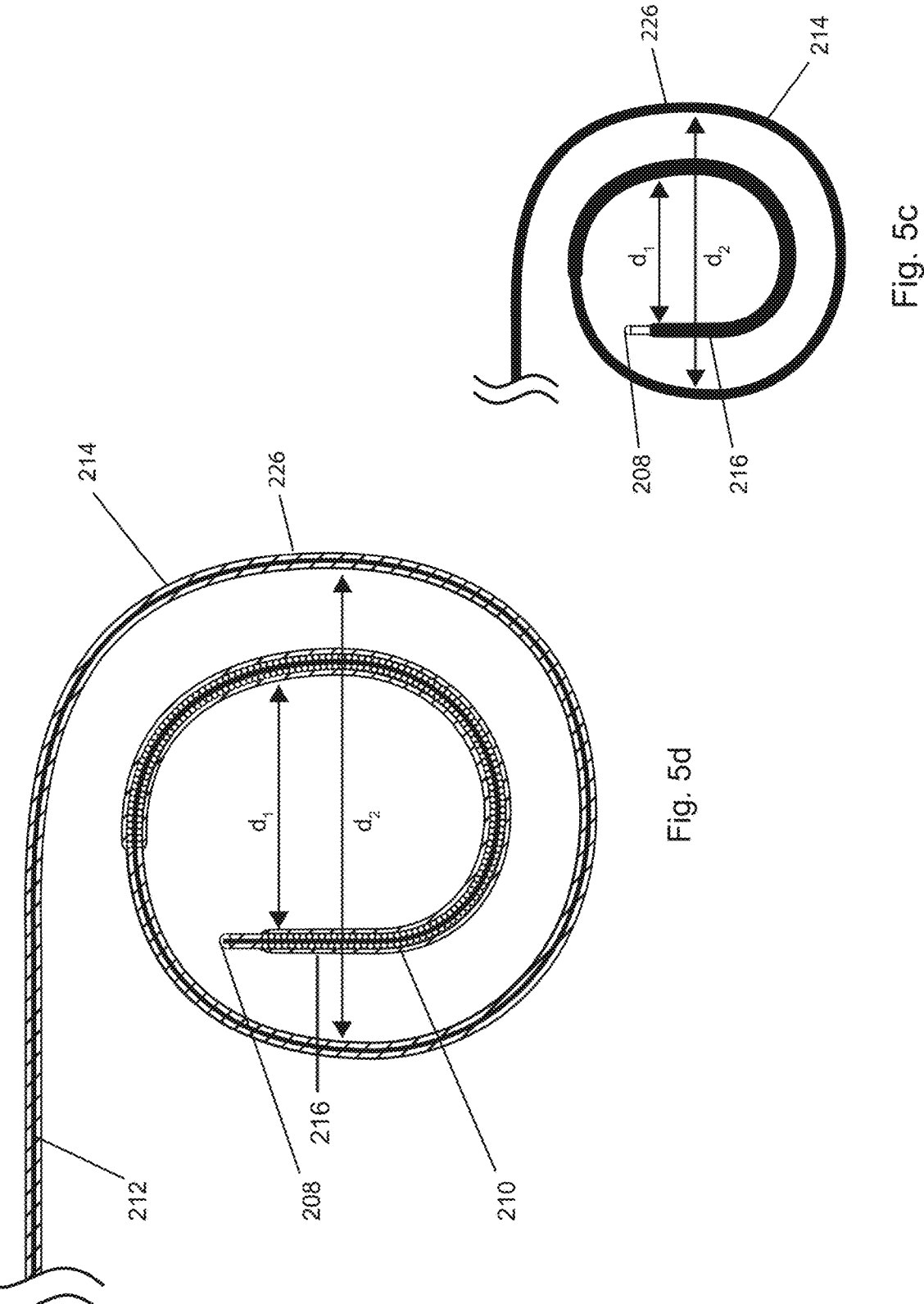
FIG. 5C is an exterior view of detail "A" of FIG. 5A.
FIG. 5D is a cross section view of detail "A" of FIG. 5A.

FIG. 5C is an exterior view of detail "A" of FIG. 5A showing distal section 202. The distal section 202 includes a distal section straight portion 216 which is distal of a distal section curved portion 226. Distal section straight portion includes active tip 208. In some embodiments, a length of distal section 202 is about 30 mm to about 150+/−10 mm. In some embodiments, a length of the distal section is about 125 mm.

Distal section 202 is configured such that when it is advanced through a puncture site in tissue, such as cardiac structures, it assumes a coiled configuration whereby the active tip 208 is directed away from the tissue, and is positioned at a predetermined distanced from electrically insulated portions of distal section 202. Distal section straight portion 216 of distal section 202 advances forward along a substantially straight path (the "axis of advancement") immediately after puncturing tissue and prevents the guidewire from immediately curling back on itself in order to potentially deliver energy a second time to the tissue site. When distal section straight portion 216 has been completely advanced out of a lumen (for example, the lumen of a dilator), distal section curved portion 226 is configured such that, upon deployment of distal section 202 from a confined state (inside the lumen) along an axis of advancement, active tip 208 curves away from the axis of advancement. For example, after puncturing a septum, the configuration of distal section 202 during and after deployment (FIG. 5C) acts to prevent the electrode (active tip 208) from directly contacting tissue on the left side of the heart, and from contacting the distal section curved portion 226 of the guidewire. Positioning the active tip 208 at a distance from distal section curved portion 226 helps to ensure that the guidewire will not be damaged if energy is delivered through active tip 208 once the coil configuration has been achieved.

The configuration of a coiled distal section 202 is shown in FIGS. 5A, 5C and 5D, which illustrate examples of an approximately 630° generally spiral-shaped curve (also known as a double pigtail curve). Distal section 202 (FIG. 5C) has an inner curve diameter d1 associated with an inner region of the 630° spiral-shaped curve and an outer curve diameter d2 associated with an outer region of the curve. Distal curves of some alternative embodiments range from about 270° to about 630°, with a specific alternative embodiment having a 270° curve (a single pigtail curve). Other alternative embodiments have curves of about 360° and about 450°. Yet other alternative embodiments have distal section 202 curves of less than 270°.

In some embodiments of the multi-function guidewire, inner curve diameter d1 is about 6 mm to about 30 mm, and in some embodiments is about 10 mm. In some embodiments of the multi-function guidewire, outer curve diameter d2 is about 20 to about 40 mm, and in some specific embodiments is about 22 mm.

As previously mentioned, distal section 202 is configured such that active tip 208 does not contact distal section curved portion 226. FIG. 5C illustrates an example of a distal curved section in a coiled configuration in which active tip 208 is spaced a pre-determined distance away from distal section curved portion 226. In the illustrated embodiment, active tip 208 is orthogonal (at a 90° angle) to the point along distal section curved portion 226 to which it is closest. In some embodiments, the distance of the active tip 208 from the insulated portion of the distal section 202 to which it is orthogonal (i.e. closest to) ranges from about 0.8 mm to about 4 mm. In some embodiments, the pre-determined distance of the active tip from an insulated portion of the distal section which it is closest to, is about 2.8 mm.

The pre-determined distance of the active tip from the distal section curved portion 226 of distal section 202 can also be measured relative to the diameter of the active tip. Using this method of measurement, in some embodiments the pre-determined distance of the active tip from an insulated portion of the distal section is equivalent to about 1 to about 5 times a diameter of the active tip, and in a specific embodiment is equivalent to about 4.6 times a diameter of the active tip.

Distal section 202 is substantially atraumatic. It includes a rounded electrode (active tip 208) for puncturing, not a sharp tip such as used for mechanical puncturing. Furthermore, distal section 202 is substantially flexible (i.e. floppy) so as to avoid exertion of traumatic forces on tissue (i.e. it acts as an atraumatic bumper) and distal section 202 (with the exception of the rounded electrode) is covered with a smooth layer insulation 214 (which may be anti-thrombogenic). In embodiments of the present invention, distal section 202 does not contain any sharp edges or rough surfaces.

FIG. 5D is a cross section view of distal section 202 indicated by detail "A" in FIG. 5A. Distal section 202 includes wire 212 with electrical insulation 214 thereupon, marker 210, distal section straight portion 216, and active tip 208 at the furthermost distal tip of the wire. Marker 210 surrounds a distal segment of wire 212 and electrical insulation 214 covers marker 210. Typically, active tip 208 is an electrode operable to deliver electrical energy for puncturing tissue, and is radiopaque, whereby it also functions as a visibility marker under medical imaging. In some embodiments, active tip 208 is formed by welding together a radiopaque marker band with the distal end of wire 212 to form a rounded electrode which is devoid of the layer of electrical insulation. Marker coil 210 may also be radiopaque and may comprise a helical coil surrounding wire 212. Marker coil 210 helps align the active tip with target tissue (e.g. a fossa ovalis) during tissue access and puncture procedures.

The outer layer of electrical insulation 214 covers wire 212 and marker 210. In typical embodiments, electrical insulation layer 214 is comprised of PTFE (Polytetrafluoroethylene) heat shrink. When multi-function guidewire 200 is advanced through tissue, the friction of the tissue on insulation layer 214 creates a force that could possibly cause the insulation to slide proximally relative to wire 212, but as illustrated more clearly in FIG. 5F, electrical insulation layer 214 extends distal of the helical coil 210, whereby the helical coil/marker helps to secure the layer of electrical insulation to the multi-function guidewire. Typically, marker coil 210 is welded, glued or otherwise suitably coupled to wire 212. In some embodiments, the insulation layer has a smooth outer surface to reduce the risk of thrombosis, and in some examples is antithrombogenic.

The stiffness of distal section 202 enables it to provide anchorage to prevent multi-functional guidewire 200 from inadvertently slipping out to a position proximal of a puncture site. The stiffness of distal section curved portion 226 decreases distally (i.e. it "tapers"). In some embodiments of the multi-function guidewire, the proximal end of distal section curved portion 226 has a stiffness about 550+/−10

N/m or less, and the stiffness decreases distally, without abrupt changes, such that the distal end of distal section curved portion 226 has a stiffness of about 1+/−0.5 N/m or greater, more specifically 0.88 N/m. In one example, a distal section curved portion 226 of the distal section has a stiffness of about 200 N/m at its proximal end and a stiffness of about 2.0 N/m, or more specifically 2.1 N/m, at its distal end.

In some embodiments, the stiffness of multi-function guidewire is mostly provided by wire 212, with electrical insulation 214 and marker 210 providing negligible stiffness relative to the wire. As known to one skilled in the art, the stiffness of multi-function guidewire 200 is related to (or a function of) the diameter of wire 212. In some embodiments of the multi-function guidewire 200, the wire 212 at the proximal end of the distal section curved portion 226 has an outer diameter of about 0.64 mm or less. In some examples, the wire at the distal end of distal section curved portion has an outer diameter of about 0.13 mm or more. In one example, the wire 212 of the distal section curved portion tapers distally from a proximal end outer diameter of about 0.5 mm to a distal end outer diameter of about 0.16 mm.

In typical embodiments, the elasticity and stiffness of distal section 202 make it possible for the multi-function guidewire to align with a curved lumen of a device, such as a dilator, containing the multi-function guidewire (i.e. to conform to a shape of a tubular member while positioned within a lumen of the tubular member).

Marker 210 aids in positioning the distal end of the multi-function guidewire 200, in particular, positioning active tip 208 before, during and after puncturing, and also in positioning devices that are advanced over the guidewire, such as pacemaker leads, thereby increasing the safety and efficacy of related medical procedures.

In some embodiments, marker/coil 210 is comprised of platinum and tungsten, and in one embodiment is comprised of platinum with about 8% tungsten. In most embodiments, the helical coil extends proximally from the active tip along a curve of about 180° to about 630°, and in one example along a curve of about 270°. Typically, the helical coil has length of about 15 to about 100 mm, and in one example has length of about 30 mm.

In some embodiments, the outer diameter of multi-purpose guidewire 200 (including wire 212, insulation layer 214 and coil 210, as applicable) at a proximal end of the distal section curved portion is about 0.86 mm or less, and a distal end of the distal section curved portion has an outer diameter which is about 0.59 mm or more. In one example, the outer diameter of the proximal end of distal section curved portion is about 0.72 mm and the outer diameter at the distal end of the distal section curved portion is about 0.59 mm.

Figure 5F:
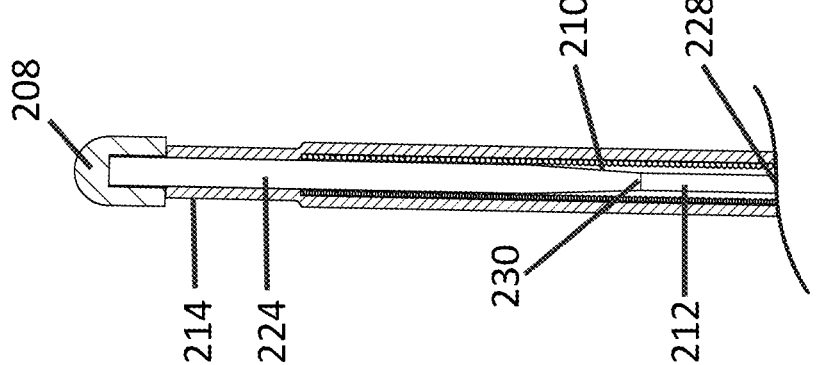
FIG. 5F is a cut-away view of section A-A of FIG. 5D.
Figure 5E:
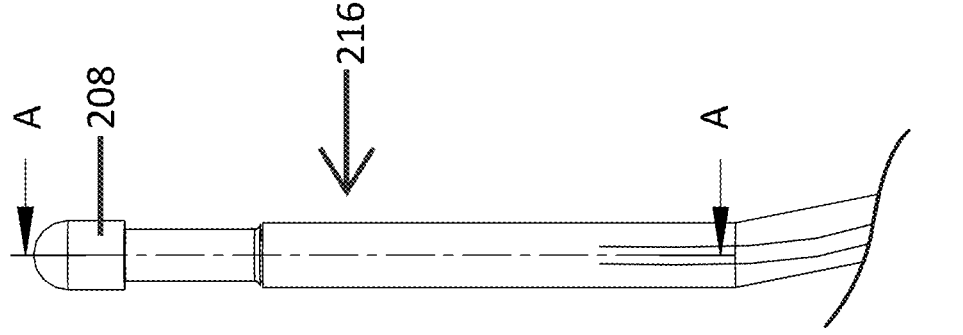
FIG. 5E is an exterior view of the distal section straight portion of a curved distal section.

FIG. 5E illustrates an exterior view of distal section straight portion 216. As shown in FIG. 5C, distal section straight portion 216 is distal of distal section curved portion 226. The distal section straight portion prevents distal section 202 from curving immediately upon exiting a lumen, for example, the lumen of a dilator. In some embodiments, distal section straight portion 216 has a larger diameter than a distal end of the distal section curved portion 226. In most embodiments, distal section straight portion has a length of about 3 to about 10 mm, and in one example distal section straight portion has a length of about 6.5 mm.

FIG. 5F shows a cross-sectional view of distal section straight portion 216 along the line A-A from FIG. 5E. FIG. 5F includes: distal section straight portion 216, the distal end 228 of distal section curved portion 226, wire 212, minimum diameter portion 230, constant diameter portion 224, and active tip 208.

Distal section straight portion 216 includes constant diameter portion 224, which is a part of wire 212, and which typically has an outer diameter ranging from about 0.13 mm to about 0.65 mm. In one particular example, the diameter at the constant diameter portion 224 is about 0.25 mm. The outer diameter of the constant diameter portion 224 is the largest diameter of wire 212 within the distal section straight portion 216. Wire 212 is has a larger diameter adjacent active tip 208 in order to withstand the heat produced by active tip 208 without being damaged.

In some embodiments, the diameter of wire 212 at the minimum diameter portion 230 is the smallest diameter of wire 212 within distal section straight portion 216, and is also the smallest diameter of wire 212 of the entire multi-function guidewire 200. The diameter of wire 212 at minimum diameter portion 230 typically ranges from about 0.13 mm to about 0.64 mm, and in one example is about 0.16 mm, and is proximal of the constant diameter portion. The outer diameter of wire 212 increases distally from minimum diameter portion 230 to constant diameter portion 224, i.e. wire 212 flares out distally (or has a reverse taper).

As previously described, active tip 208 is used for delivering energy, for example for puncturing tissue. In some embodiments, active tip 208 is comprised of platinum and iridium, and in one embodiment is comprised of platinum with 10% iridium. Typically, active tip is dome-shaped. In some embodiments of the multi-function guidewire, the active tip 208 has a diameter ranging from about 0.4 to about 0.7 mm, and in one example has a diameter of about 0.6 mm. Typically, active tip 208 has a length ranging from about 0.75 mm to about 1.5 mm, and in one embodiment has a length of about 0.8 mm.

Referring back to FIG. 5B, proximal section 206 includes proximal section curved portion 232 and proximal section straight portion 215, which includes exposed portion 212a of wire 212.

While proximal section 206 is typically biased to a coiled configuration, it is also flexible which allows it to be uncoiled. Typically, wire 212 has a constant diameter throughout the proximal section 206, with typical embodiments of the wire at proximal section curved portion 232 having an outer diameter ranging from about 0.13 mm to about 0.64 mm, and in one example having an outer diameter of about 0.38 mm. In some embodiments, the proximal section of the guidewire/elongate member (i.e. wire 212 as well as insulation layer 214) has an outer diameter of about 0.60 mm.

In some embodiments, proximal section 206 is curved in the same plane as distal section 202, i.e. the curves are coplanar. Having coplanar proximal and distal curves is advantageous in that, for example, when the distal section extends out of a dilator within the body, the orientation of the proximal curve outside of the patient's body can be used to ascertain the orientation of the distal curve, which itself may not be directly visualized, in order to aid in positioning.

The configuration of proximal section straight portion 215 aids in loading over-the-wire devices onto the multi-function guidewire 200. To assist in providing this functionality, the proximal section straight portion 215 is elongated and has a diameter less than or equal to the rail section. In some embodiments, proximal section straight portion 215 has a length of about 5 to about 50 mm, and in one embodiment, has a length of about 25 mm. To provide for greater user safety when loading devices onto the multi-function guidewire, proximal section straight portion 215 has a rounded tip.

An additional function of proximal section straight portion 215 is provided by its relatively small diameter. Due to its size, proximal section straight portion 215 is operable to puncture tissue mechanically (i.e. without the delivery of electrical energy). This allows a user the option to potentially attempt both mechanical and electrical punctures using a single device. For example, a user may attempt mechanical puncture using the proximal end of the device and, if unsuccessful, the user may withdraw the device and insert the distal end to attempt electrical puncture. In some embodiments, the elongate member/guidewire 200 at the proximal section, including wire 212 and insulation 214, has an outer diameter of about 0.86 mm or less, with one embodiment having an outer diameter of about 0.60 mm or less.

Multi-function guidewire 200 includes exposed portion 212a of wire 212 to allow for coupling to a source of electrical energy, for example using a removable push-button connector placed over exposed portion 212a. In some embodiments, exposed portion 212a has a length ranging from about 5 to about 15 mm, and in one example, has a length of about 10 mm.

Some embodiments of multi-function guidewire 200 include transitional portion 222 between the proximal section 206 and rail section 204 to avoid having an abrupt change in diameter, for example to avoid structural weaknesses. In some embodiments, the transitional portion 222 defines a length ranging from about 15 mm to about 100 mm, with one embodiment defining a length of about 25 mm. The proximal end of transitional portion 222 has an outer diameter ranging from about 0.35 mm to about 0.86 mm and the distal end has an outer diameter of about 0.58 mm to about 1.12 mm. One particular embodiment has a minimum outer diameter of about 0.60 mm and a maximum outer diameter of 0.86 mm.

In a specific embodiment of multi-functional guidewire 200, active tip 208 is primarily comprised of platinum, with 10% iridium; marker 210 is a helical coil primarily comprised of platinum, with 8% tungsten; and each of the proximal section 206, rail section 204, and distal section 202 are comprised of a 304V stainless steel wire 212 (spring tempered) with PTFE heat shrink insulation (electrical insulation 214) thereupon. Stainless steel wire 212 has adequate stiffness to provide pushability to multi-functional guidewire 200 and is also an efficient electrical conductor.

In this specific embodiment, active tip 208 has a length of about 0.8 mm and a diameter of about 0.024 inches (~0.61 mm); the wire 212 and active tip 208, combined, extend 2 mm beyond the distal end of marker 210; and marker 210 has a length of about 3 cm. Furthermore, distal section straight portion 216 has a length of about 6 to 10 mm and a diameter of about 0.018 to 0.0225 inches (0.45 to 0.57 mm)); distal section 202 has an inner curve diameter d1 of about 1 to 3 cm and an outer curve diameter d2 of about 2 to 4 cm (FIG. 5C); the diameter of rail section 204 adjacent the distal section 202 is 0.029 to 0.035 inches (0.74 to 0.89 mm).

The specific embodiment further includes wire 212 of distal section 202 having a length of 15 cm and tapering over the 15 cm segment of the wire from 0.025 inches (0.64 mm) to 0.006 inches (0.15 mm) at the tip of wire 212. The tip of wire 212 has a length of 5.5 mm and a diameter of 0.010 inches (0.25 mm) over the 5.5 mm length. The point along wire 212 that is 15 cm from the distal tip of distal section 202 (i.e. the part of distal section 202 with the largest diameter of wire 212) has a proximal stiffness (force/displacement) of about 552 N/M. In this embodiment, active tip 208 is welded to wire 212. The distal tip of marker coil 210 is 2 mm proximal from active tip 208 and has length of 30 mm. Electrical insulation 214 is comprised of PTFE heat shrink and has a wall thickness of 0.004 inches (0.10 mm).

Furthermore, in this specific embodiment, rail section 204 has a length of about 120 cm; and the wire 212 within the rail section has a diameter of about 0.635 mm±0.008 and stiffness of about 552 N/M. Proximal section 206 has a length of about 525 mm±1.5, including a tapered section of about 2.5 cm (tapering down from the rail section), and the wire 212 of proximal section 206 has a diameter of about 0.381 mm±0.008. The overall length of wire 212 is 1800 mm±2.

Some alternative embodiments of multi-functional guidewire 200 comprise a straight proximal section 206 and/or a J-shaped distal section 202.

In alternative embodiments of the disclosed methods (described further hereinbelow), mechanical wires are used for puncturing. The mechanical wires typically have a distal part/portion/section that is J-shaped to prevent accidental punctures and trauma by a sharp distal tip. Some alternative mechanical wire embodiments have a distal part that is coiled, while others have a straight distal part.

Methods

A first broad aspect of a method of accessing a chamber of a patient's heart using a superior access approach comprises the steps of: (a) advancing a steerable device through a patient's vasculature, from a superior approach, into a heart of a patient, the steerable device defining a lumen and containing a dilator within the lumen; (b) articulating the steerable device to manipulate a distal portion of the dilator to position the dilator substantially adjacent a tissue; and (c) advancing the dilator through a puncture in the tissue. The procedure is performed using forms of imaging known to those skilled in the art.

Figure 6A:
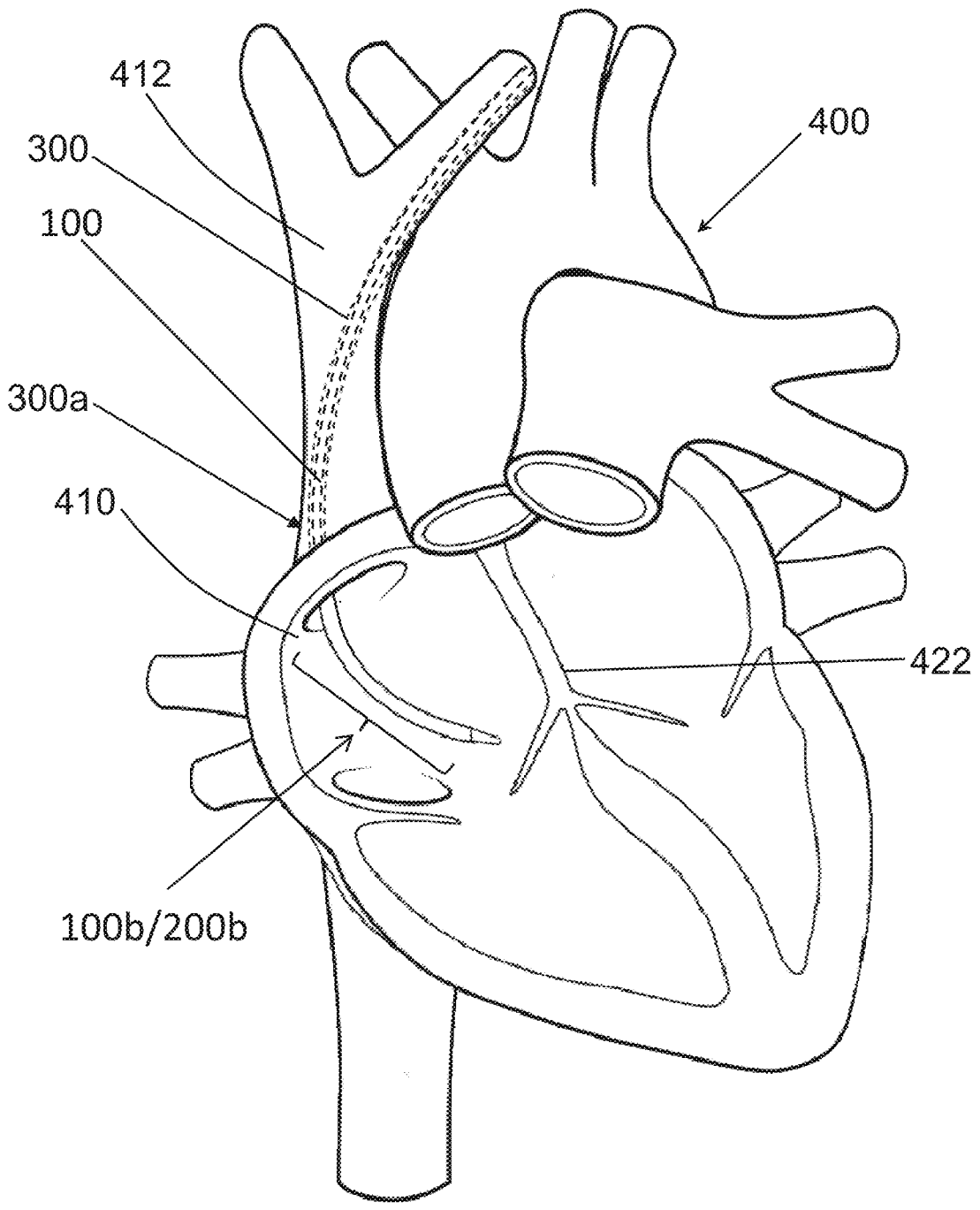
FIGS. 6A-6D illustrate a wire and dilator used in conjunction with a steerable sheath, in accordance with embodiments of the present invention.

With reference now to FIG. 6A, in a particular embodiment, as described herein, the steerable sheath 300 may be used to guide the dilator 100 to reach an area of the heart 400, in order for example to perform a transseptal puncture. In one such example, a guiding introducer or apparatus such as an introducer sheath may be advanced through the vasculature. A guide-wire may then be advanced through the introducer sheath and advanced through the vasculature, for example the superior vena cava 412, to be positioned within the right atrium 410. In some embodiments, the guide wire may be advanced without the use of an introducer sheath. A dilator 100, in accordance with an embodiment of the present invention, may then be inserted through the steerable sheath 300 forming a dilator and sheath assembly, or in other words a steerable sheath assembly 300a.

Dilator 100 comprises a flexible intermediate region 100b terminating at a rigid distal end region 100a. In the specific example shown, the dilator 100 additionally has a rigid proximal region 100c, as described previously, that helps minimize the risk of the dilator buckling as it is inserted into the steerable sheath 300. (Alternatively, a dilator 100 may be provided with a softer proximal portion 100c.) The dilator 100 is usable with a steerable sheath 300, as described previously herein above. The steerable sheath 300 defines a lumen there-through for receiving the dilator 100 and further comprises an articulating portion or deflectable region 200b that terminates in a sheath distal end. In some embodiments, the steerable sheath 300 and dilator 100 may be provided as a steerable sheath kit.

Once the dilator 100 is inserted through the steerable sheath 300, the dilator 100 extends through the sheath lumen with the distal end region 100a of the dilator extending beyond the sheath distal end. Thus, in some embodiments, the dilator 100 is inserted through the steerable sheath 300 prior to the step of inserting the steerable sheath 300 through the vasculature, and the steps of inserting and advancing the dilator 100 are performed substantially simultaneously with the steps of inserting and advancing the steerable sheath 300. Once assembled, the dilator 100 and the steerable sheath 300 are configured to co-operate with one another such that the flexible intermediate region 100b of the dilator 100 corresponds to the articulating portion or deflectable region 200b of the steerable sheath 300 during use.

In alternative embodiments, the steps of inserting and advancing the steerable sheath 300 may be performed prior to the steps of inserting and advancing the dilator 100. In a specific example, the steerable sheath 300 may initially be advanced into the right atrium 410, with a catheter or any other dilator inserted there-through, such as a second dilator. The catheter or second dilator may then be swapped out with the flexible dilator 100. That is the catheter or second dilator may be removed and the dilator 100 may be inserted through the sheath and advanced into the right atrium. In still further alternative embodiments, the steps of inserting and advancing said dilator 100 may be performed prior to the steps of inserting and advancing said steerable sheath 300, which for example, may be advanced over the dilator 100.

Figure 6B:
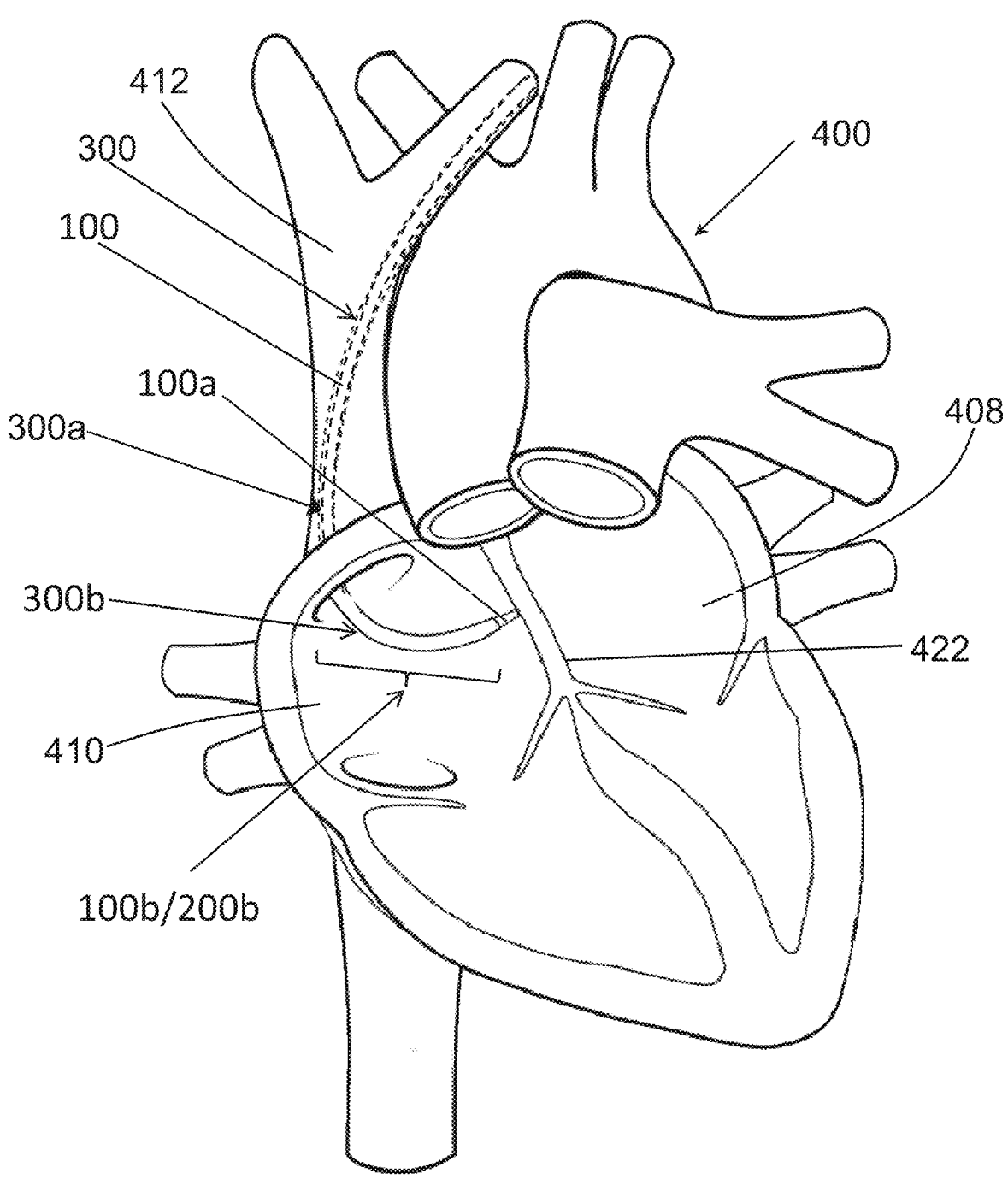
Figure 6C:
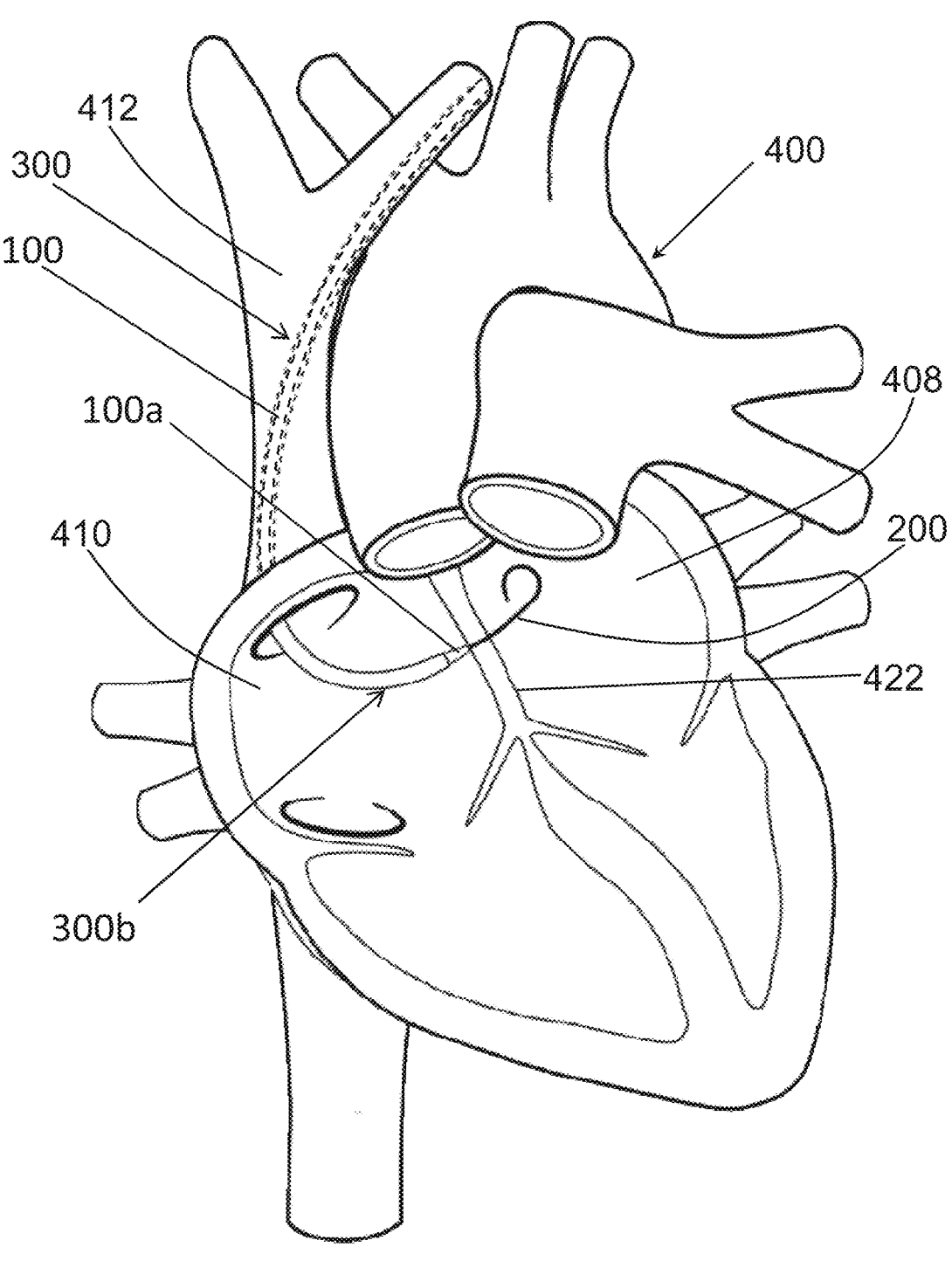

After positioning the steerable sheath assembly 300a within the right atrium 410, the initial guide-wire is swapped out with an RF guide-wire or other energy delivery device (such as RF guidewire 200 visible in FIG. 6C). Referring now to FIG. 6B, the steerable sheath 300 is then actuated to allow the steerable sheath 300 to achieve a desired deflection angle to position the dilator distal end region 100a at a desired location within a region of tissue, within a patient's body, for example a desired location within the septum 422 of the heart 400 (in some examples, more specifically, at the fossa ovalis region of the septum 422). The dilator 100 provides a flexible intermediate region 100b that does not hinder the ability of the steerable sheath 300 to curl or curve and as such allows the articulating portion or deflectable region 200b of the steerable sheath 300 to deflect upon actuation to position the dilator 100 and the RF guide-wire as desired. As such, the steerable sheath 300 is able to reach its intended curvature, as shown by path 300b, upon actuation, to position the distal end region 100a of the dilator 100 as well as a distal end of the RF guide-wire at the septum 422. Using a dilator lacking such a flexible intermediate region may result in the steerable sheath not being able to achieve the required or intended curvature, whereby the steerable sheath assembly may be limited to the curvature shown in FIG. 6A.

Additionally, as outlined previously, the dilator 100 is essentially a straight dilator that is lacking a curve. As a result the dilator 100 does not interfere with the curvature of the steerable sheath 300 by imparting a curvature to the steerable sheath 300. Thus, the lack of curvature in the dilator 100 in conjunction with the flexible intermediate region 100b, additionally aids in allowing the steerable sheath 300 to attain the required deflection angle or curvature to position the dilator distal end region 100a as well as the RF guide-wire at the septum 422.

Figure 6D:
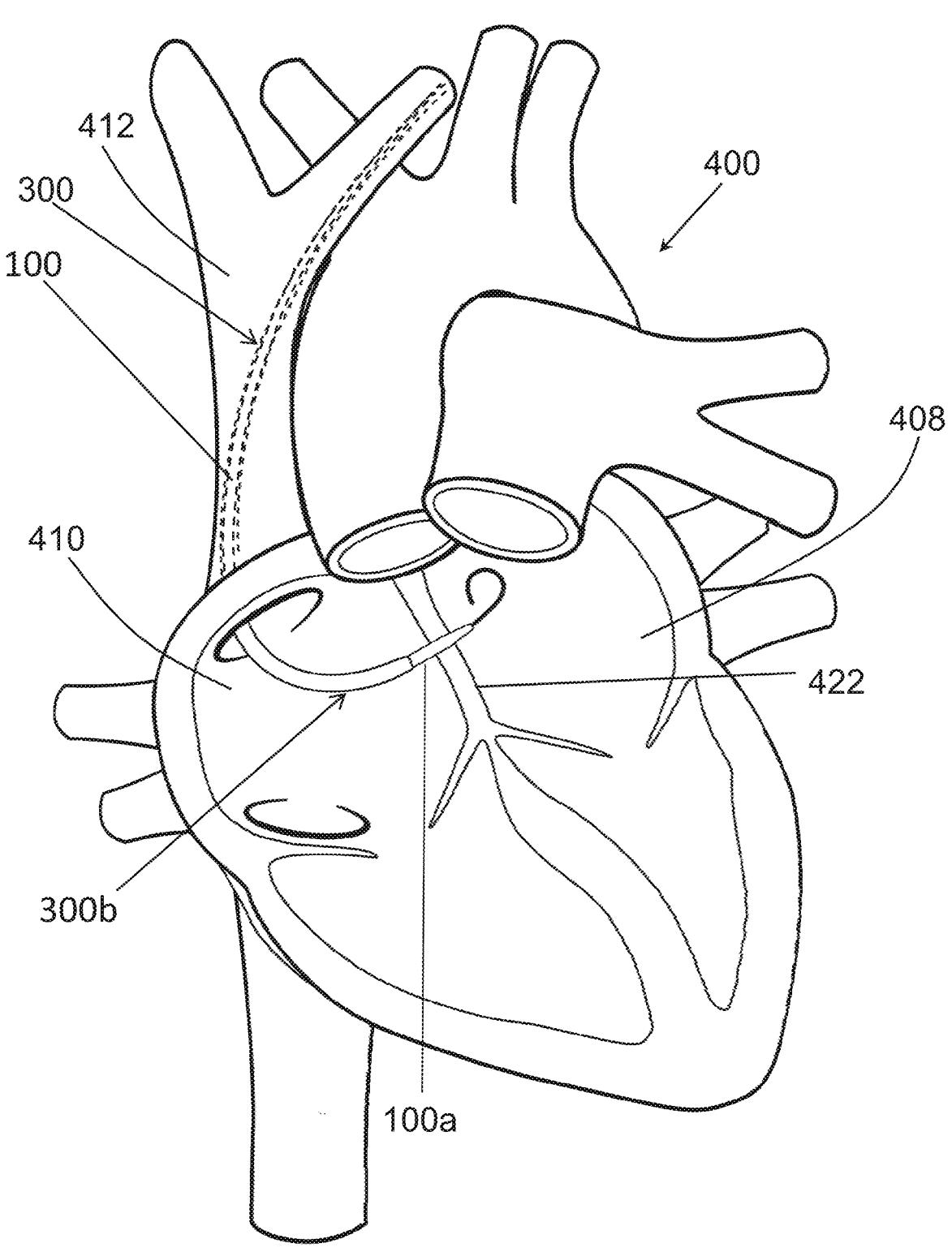

With reference now to FIG. 6C, once the distal end region 100a of the dilator 100 has been positioned at the septum 422, a transseptal puncture may then be performed, for example by using a puncturing device as described hereinabove. In one embodiment, as shown, the puncturing device comprises the RF guidewire 200 (that was previously positioned within the steerable sheath assembly 300a) which may then be activated to deliver RF and be advanced across the septum 422 to create the puncture. The guidewire 200 may then be advanced into the left atrium 408 of the heart 400, as shown in FIG. 6C. The dilator 100 may then be advanced over the guidewire 200 through the septum 422 in order to dilate the transseptal puncture site, as shown in FIG. 6D, for example in order to facilitate tracking of other devices through the puncture site. The steerable sheath 300 and the dilator 100 may then be withdrawn and the other devices may be advanced over the guidewire 200, for example, to perform a procedure within the heart.

FIGS. 7A to 7G illustrate the steps of an alternate embodiment of a method for gaining access to the left side of a heart. Anatomical features illustrated in FIG. 7A include: heart 400, left ventricle 402, right ventricle 404, mitral valve 406, left atrium 408, right atrium 410, superior vena cava 412, inferior vena cava 414, aorta 416, and brachiocephalic veins 418.

Figure 7A:
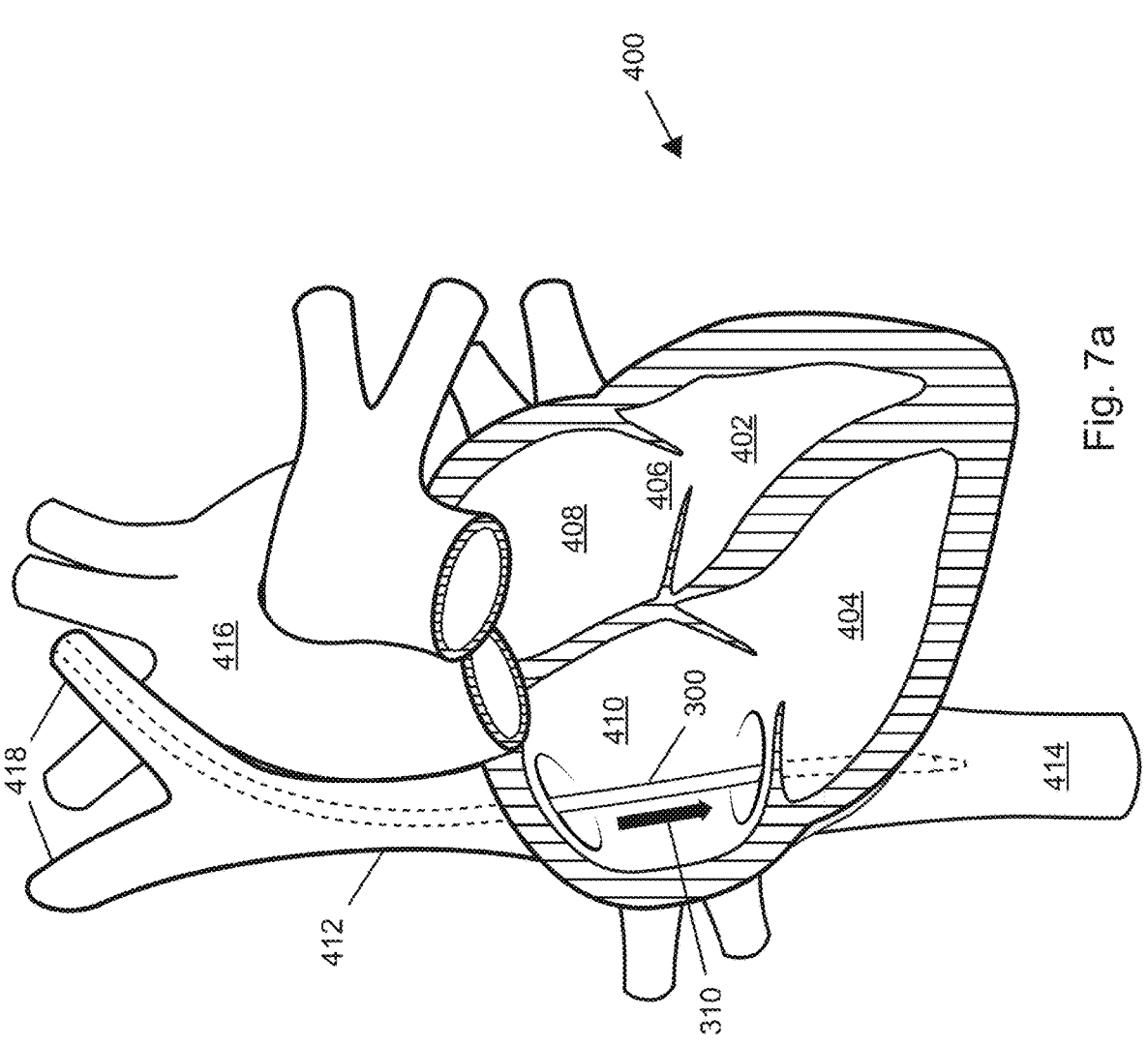
FIGS. 7A-7G illustrate a further embodiment of a method of using a system in accordance with embodiments of the present invention to perform a transseptal puncture from a superior access approach.
Figure 7B:
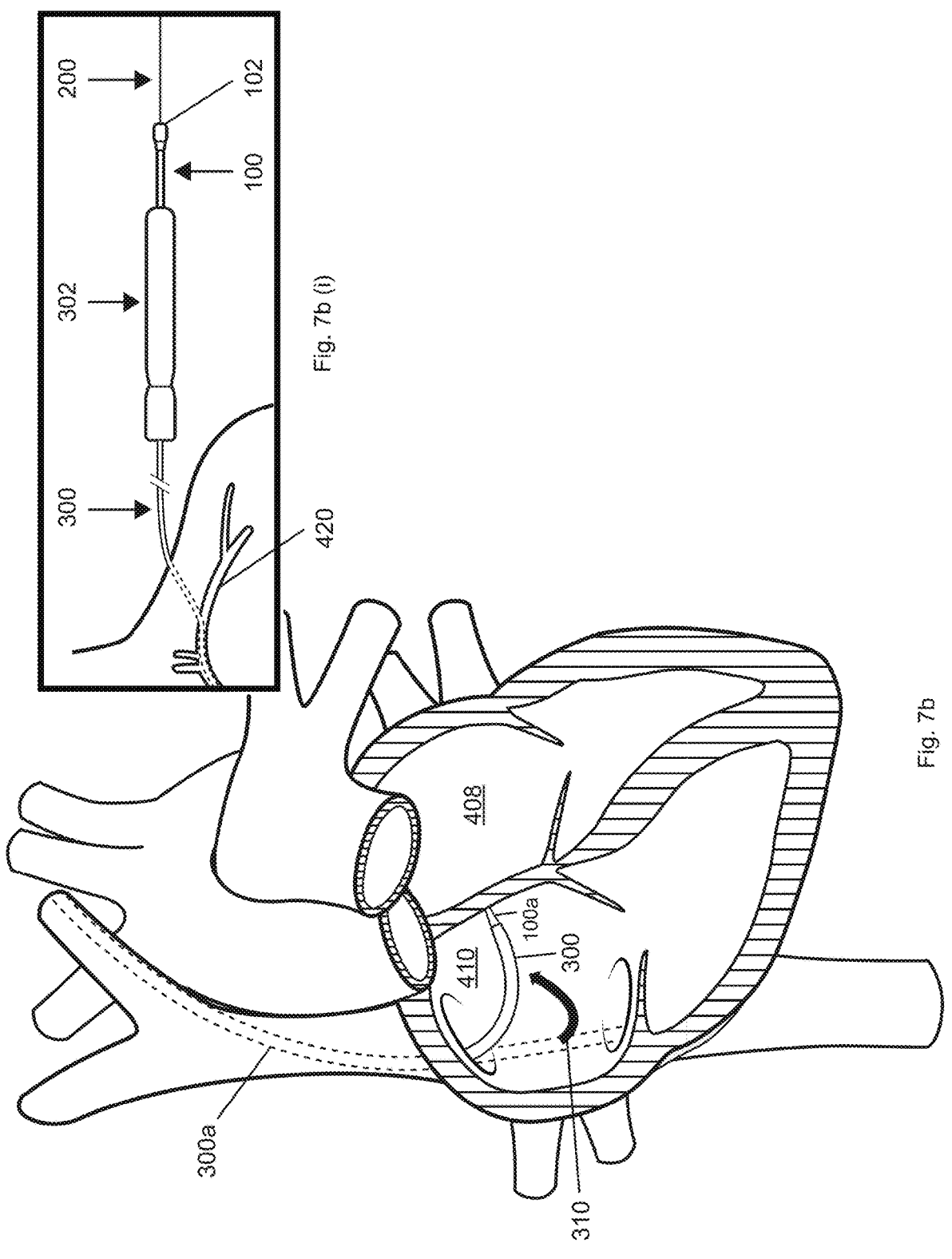

FIG. 7B(i) shows access being gained through the left subclavian vein 420, which is superior (i.e. above) to heart 400. In some alternative embodiments a large diameter, short length introducer (not shown in drawings), known to those skilled in the art, is secured at the left subclavian access site to accommodate the steerable sheath. In the embodiment of FIG. 7B(i), steerable sheath 300 is advanced through left subclavian vein 420. Steerable sheath 300 is controlled using steerable sheath handle 302. Dilator 100, which includes dilator hub 102, is inserted into steerable sheath 300. Typically dilator 100 and steerable sheath 300 are locked together before being advanced through the vasculature to form a steerable sheath assembly. FIG. 7B(i) also shows that a wire 200 is inserted into dilator 100.

As described above in the above embodiment of a method of the present invention, step (a) is for advancing a steerable device having a lumen and containing a dilator within the lumen, from a superior approach, into a heart of a patient. To arrive at the configuration of FIG. 7A, a steerable device, steerable sheath 300, is advanced through superior vena cava 412 and right atrium 410, as indicated by sheath movement arrow 310, and temporally positioned in inferior vena cava 414. FIG. 7A illustrates the position of apparatus upon a completion of step (a). From the position shown in FIG. 7A, steerable sheath 300 and dilator 100 are slightly withdrawn to position the dilator's distal tip 106 in right atrium 410. In alternative embodiments of the method, steerable sheath 300 is not advanced into inferior vena cava 414, but instead, advancement is stopped when the distal tip of the steerable sheath is still in right atrium 410. Steerable sheath 300 defines a lumen and contains a dilator 100 within the lumen. Typically, the physician selects the dilator and steerable sheath to match the outer diameter of dilator 100 with the inner diameter of steerable sheath 300 (i.e. so that the dilator fits snugly within the sheath or, put differently, that the dilator is cooperatively fitted to the sheath) so that the dilator may provide support for the sheath to prevent the sheath from buckling when making sharp turns, such as when, for example, steering the sheath towards the atrial septum after the sheath is advanced through the superior vena cava. Furthermore, matching the outer diameter of dilator 100 with the inner diameter of steerable sheath 300 facilitates smooth advancement through the vasculature by avoiding and/or reducing scraping of tissue.

Once the dilator's distal tip 106 is advanced into right atrium 410, the tip is positioned within the right atrium using the steerable sheath. The portion of the dilator shaft 104 of dilator 100 inside of right atrium 410 (and within steerable sheath 300) is flexible enough to be cooperatively steered by the sheath i.e. sheath 300 can manipulate dilator shaft 104 to the required angle to contact tissue without the dilator restricting the sheath's range of motion. Only the portion of dilator shaft 104 within the part of steerable sheath 300 that is being bent for the "U-turn" from the superior vena to contact the atrial septum needs such a high degree of flexibility: the disclosed method can still be performed even if other portions of dilator shaft 104 (not inside the right atrium) are relatively less flexible (i.e. more rigid) than the highly flexible portion.

Step (b) of the method is for the physician articulating the steerable device (steerable sheath 300), in the direction indicated by sheath movement arrow 310, to cooperatively manipulate a distal portion of the dilator 100 and thereby position the dilator substantially adjacent a tissue. The dilator is manipulated to arrive at the position shown in FIG. 7B. For the sake of simplicity, some embodiments of the method use a unidirectional sheath: the direction of deflection is known before the procedure such that a bi-directional sheath is not required, although it may be used as well.

FIG. 7B also shows dilator 100 slightly extended from steerable sheath 300 and touching a tissue site (atrial septum 422). A flexible elongate puncture member (medical device/guidewire 200) is located within the dilator's lumen when the physician adjusts steerable sheath 300 to cooperatively position dilator 100. Typically, the elongate puncture member 200 is positioned to be close to, but not contacting, the fossa ovalis of the atrial septum. The embodiment of guidewire 200 of FIG. 5D has radiopaque active tip 208 and radiopaque helical marker 210, which when positioned towards the front of the dilator aid in positioning dilator 100 under imaging.

Figure 7C:
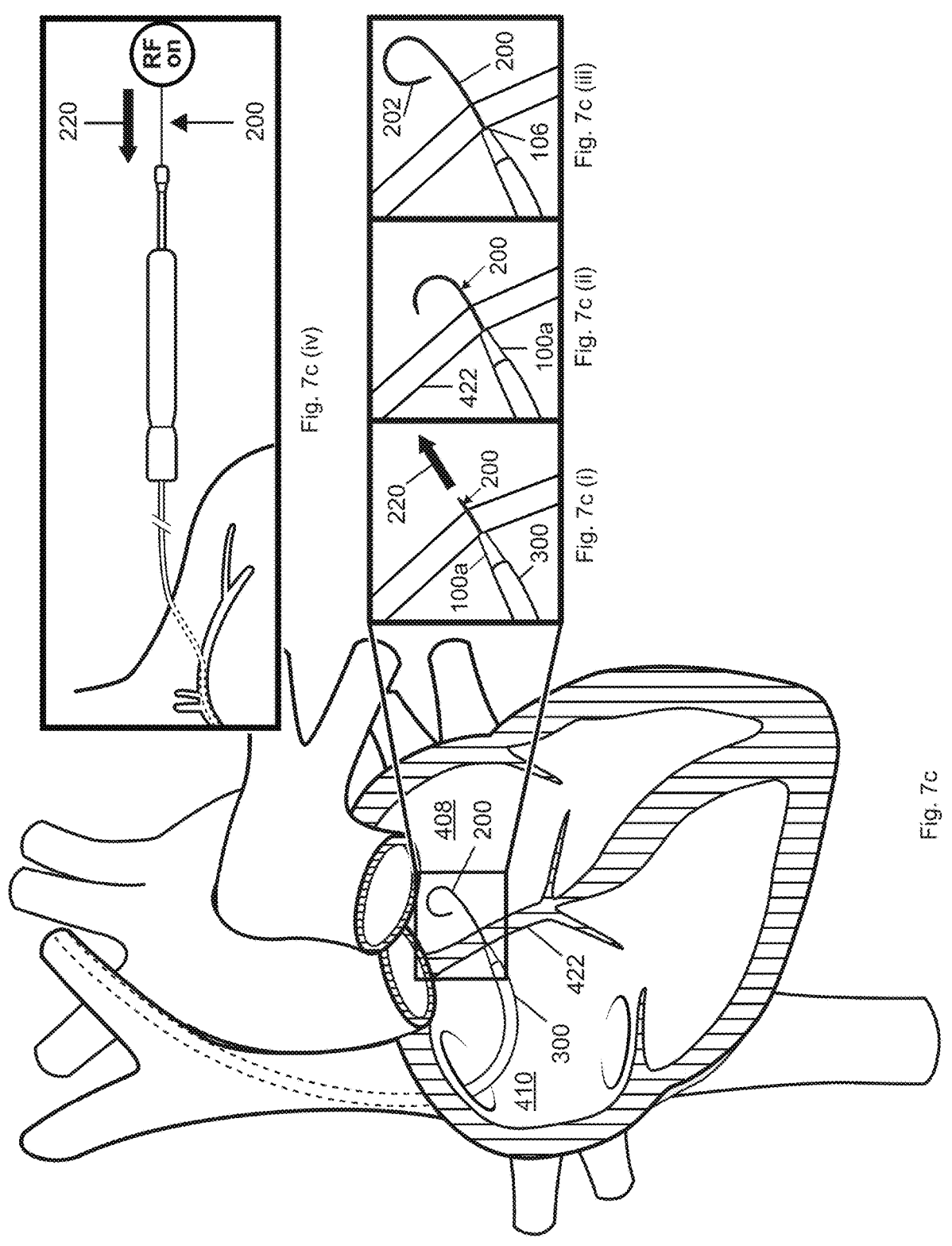

Typical embodiments of a method of the invention comprise the dilator having a lumen (not shown in drawings) and containing an elongate puncture member therein, and the method including between steps (b) and (c), advancing the elongate puncture member and puncturing the tissue. While the method is not limited to any particular type of tissue, in the illustrated embodiment the tissue is a septum of the heart and the method comprises, between steps (b) and (c), advancing an elongate puncture member (wire 200) and puncturing atrial septum 422, as illustrated in FIGS. 7C(i) to 7C(iii). In FIG. 7C(i), the distal tip of dilator 100 is tenting the atrial septum 422 while the wire is advanced in the direction of wire movement arrow 220. The steerable device (steerable sheath 300) is used to position dilator 100 for tenting the septum dilator under imaging. Tenting ensures the dilator is properly positioned and in contact with the septum. FIG. 7C(iv) shows wire being advanced from the proximal end (the end toward the physician) and indicates diagrammatically the use of RF energy. FIG. 7C(ii) shows wire 200 having just punctured atrial septum 422. The distal portion/part of the wire is comprised of a material with shape memory and it curves back as it is extended into left atrium 408. FIG. 7C(iii) shows the wire further extended and curving back approximately 270° into a "pig-tail" configuration (although, as described hereinabove, this coil may typically traverse between 270° and 630°). FIG. 7C shows heart 400 with the wire 200 that has punctured the septum and is in the position of FIG. 7C (iii). As previously noted, curved distal part 202 acts to prevent the electrode (active tip 208) from directly contacting tissue on the left side of the heart.

In some embodiments of the method aspect of the present invention, the elongate puncture member is an energy delivery device, and puncturing tissue between steps (b) and (c) comprises delivering energy through the energy delivery device (e.g. a distal end of the energy delivery device) to puncture the tissue. In some such embodiments, the energy delivery device is operable to deliver electrical energy, and in some specific embodiments, the electrical energy is in the RF range.

In some other embodiments, the elongate puncture member is a mechanical wire with a sharp tip, and puncturing tissue between steps (b) and (c) comprises advancing the mechanical wire such that the sharp tip of the mechanical wire punctures the tissue.

After wire 200 has punctured the septum, the physician proceeds to step (c) of the method. Step (c) is for advancing the dilator through a puncture in the tissue. The first broad aspect of the method includes the use of a hybrid dilator having a flexible intermediate region 100b that can be bent from a superior approach to approach the septum, a bend of about 180° (i.e. a U-shaped turn), with the hybrid dilator also having a distal tip that is sufficiently hard to provide for dilating tissue without deformation of the taper. The use of the hybrid dilator makes it unnecessary to use a soft dilator for steering and bending for the U-shaped turn, and then changing to a stiffer dilator for crossing the septum, whereby the hybrid dilator reduces the number of steps in the procedure by eliminating the steps of withdrawing a soft dilator and advancing a hard dilator.

Figure 7E:
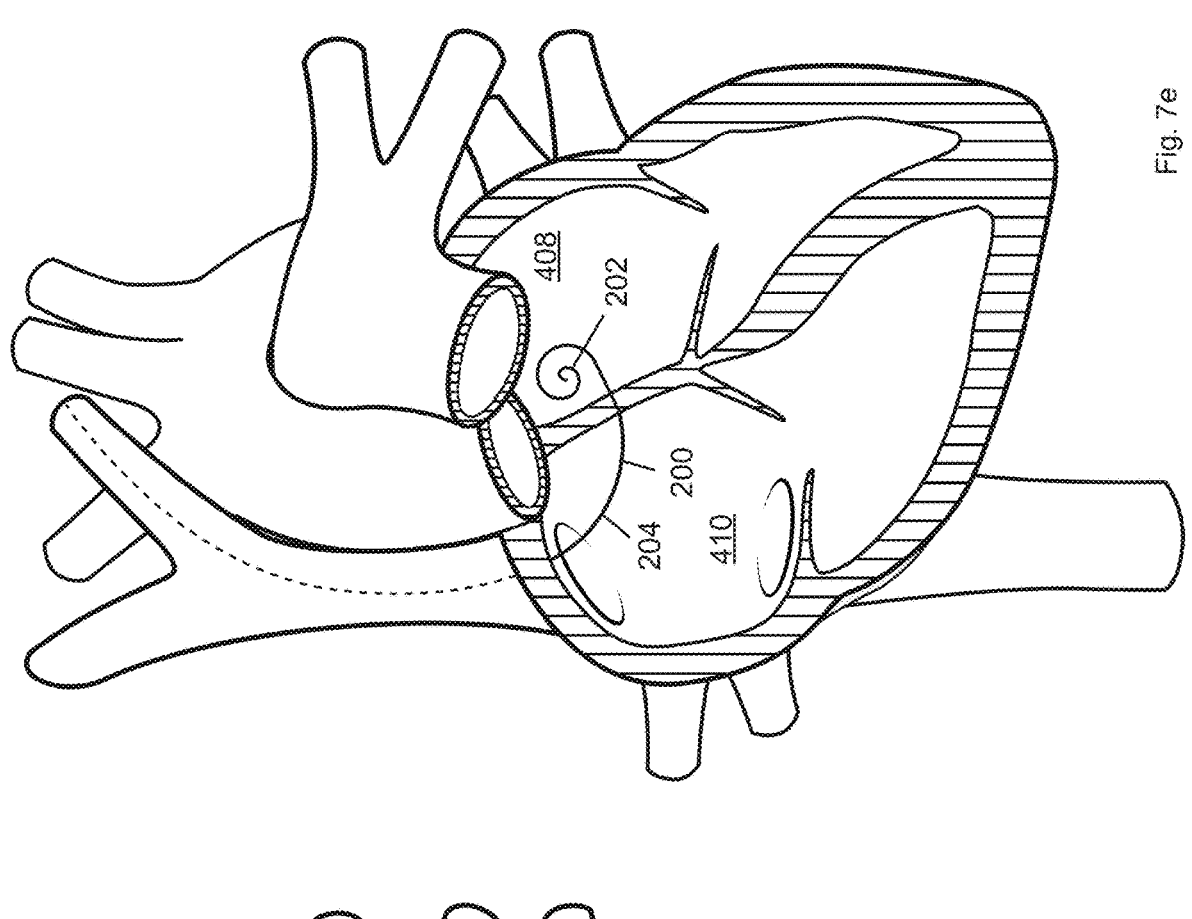
Figure 7D:
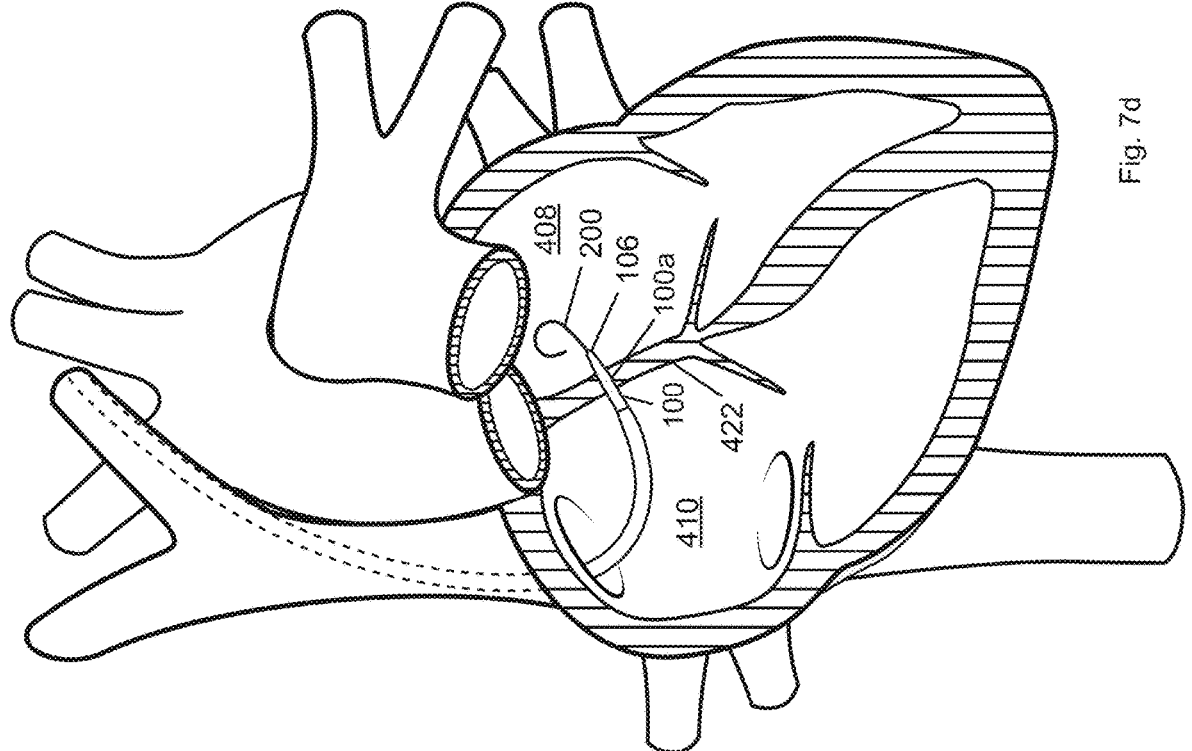

FIG. 7D shows a positioning of the dilator after completion of step (c) of the method (advancing the dilator through a puncture in the tissue). Distal tip 106 of dilator 100 is comprised of hard (shape retaining) material that pushes aside tissue as dilator 100 is advanced. A portion of flexible intermediate region 100b is shown extended from steerable sheath 300 inside of right atrium 410 in FIG. 7C. Typically, advancement of dilator 100 is stopped when maximum dilation is achieved; resulting in the dilator being positioned such that a distal portion of dilator's distal tip 106 is in left atrium 408 and a portion of distal tip is in right atrium 410. In alternative embodiments of the method, the dilator is further advanced so that all of distal tip 106 is in the left atrium, such as, for example if the physician wants to ensure that maximum dilation has been achieved.

Some embodiments of the method aspects of the present invention further comprise a step (d) of withdrawing the elongate puncture member (and advancing an anchor wire until the anchor wire bridges (crosses) the septum and a right atrium to thereby provide a bridge between the superior vena cava and the left atrium (put differently, the anchor wire bridges the septum between the right and left atria). After an anchor wire is advanced, some embodiments further comprise a step (e) of withdrawing the dilator and sheath. FIG. 7E illustrates an installed anchor wire (wire 200) with the dilator and sheath withdrawn. As previously described, curved distal part 202 of wire 200 provides anchorage to prevent wire 200 from inadvertently slipping back into the right atrium. The anchor wire is sufficiently stiff that it may, by itself, provide a rail for advancing medical devices into the left atrium. Such medical devices are selected at the discretion of the physician and can include, at least, ablation catheters and pacing leads (e.g. for left ventricular endocardial pacing). As described hereinabove as well as hereinbelow, in an exemplary embodiment of a method of the present invention, a single wire may be utilized for both the puncturing step as well as for anchoring in the left atrium by using a hybrid medical device, such as multi-function guidewire 200, to puncture the tissue site and provide a rail (as well as an anchor) through the puncture site.

Figures 7F, 7G:
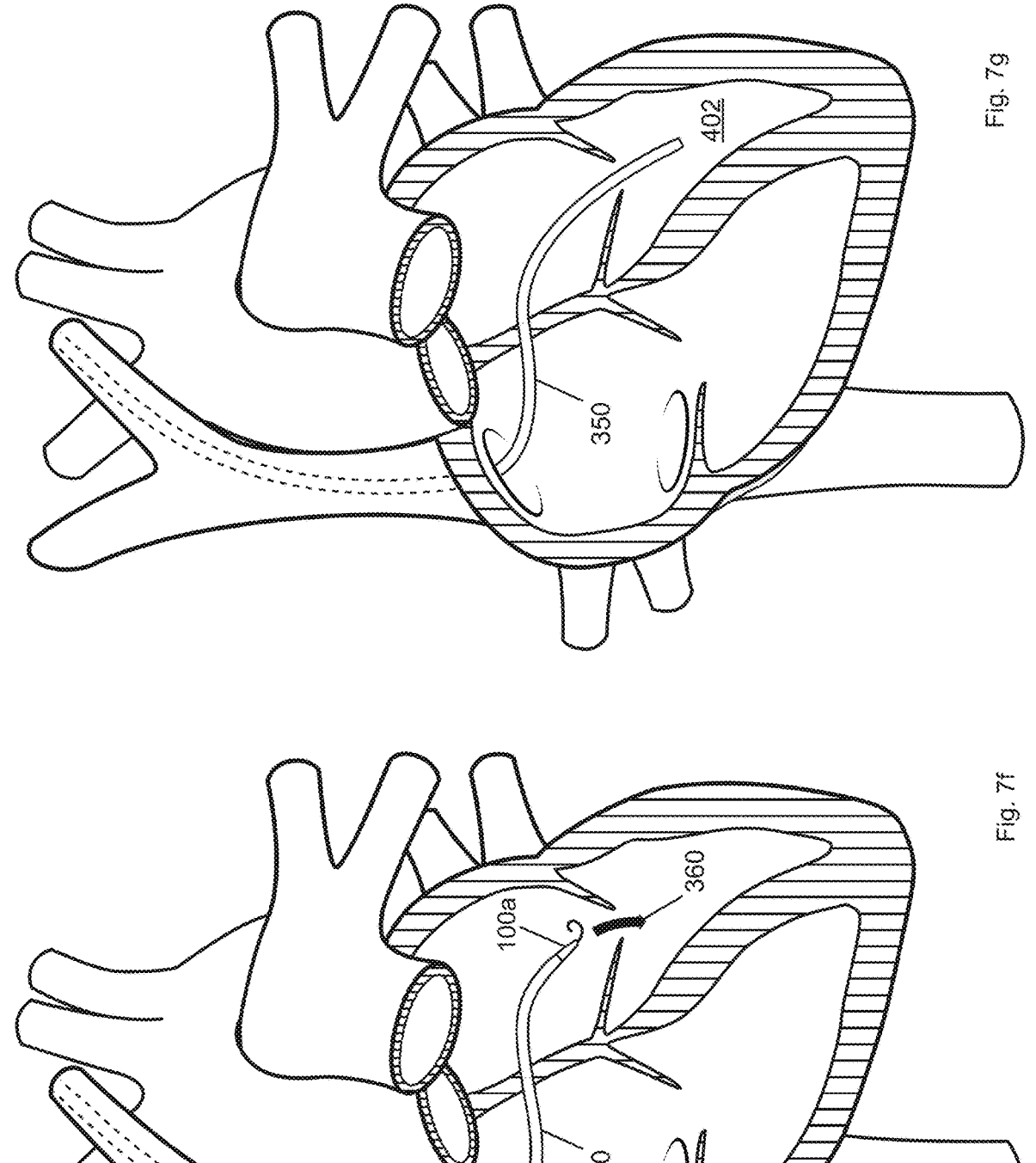

Some embodiments of the method aspect further comprise a step (f) of advancing a lead delivery catheter 350 (and possibly a lead delivery dilator, if dilator 100 may not be used for the stated purpose), configured for delivering leads (such as pacemaker leads), into the left atrium of the heart, as shown in FIG. 7F. As previously described, other medical devices are advanced/implanted in some alternative embodiments.

Some embodiments further include a step (g) of withdrawing the wire 200 (as well as any dilators, including a lead delivery dilator). Some such embodiments further comprise a step (h) of advancing the lead delivery catheter 350 as indicated by catheter movement arrow 360 (FIG. 7F), to thereby position the distal end of lead delivery catheter 350 in left ventricle 402, as shown in FIG. 7G.

For some embodiments of this method aspect, a stiff introductory wire (rather than a hybrid wire such as guidewire 200) is used. Such embodiments comprise: prior to step (a), advancing the stiff introductory wire into the right atrium; and step (a) includes advancing the steerable sheath and the dilator over the stiff introductory wire; and between steps (b) and (c), the stiff introductory wire is withdrawn and the elongate puncture member is advanced to puncture the septum. In some such embodiments, the stiff introductory wire is comprised of stainless steel. Typically, an introductory wire has an atraumatic tip that is generally J-shaped.

In some embodiments, as noted above, a stiff introductory wire is not utilized; rather, a hybrid wire such as described above may be utilized. Such embodiments comprise: prior to step (a), the wire/elongate puncture member is advanced into the right atrium; and step (a) includes advancing the steerable sheath and the dilator over the wire/elongate puncture member.

A further broad aspect of the method of accessing a chamber of a patient's heart using a superior access approach is described below. The method comprises the steps of: (a) advancing a steerable device through a patient's vasculature, from a superior approach, into a heart of a patient, the steerable device defining a lumen and containing an elongate puncture member within the lumen; (b) articulating the steerable device to manipulate a distal portion of the elongate puncture member for positioning the puncture member substantially adjacent a tissue; (c) creating a puncture in the tissue using the puncture member; and (d) advancing a dilator over the puncture member through the puncture.

This broad aspect relates to the concept of reducing or minimizing the number of steps in a procedure by using multifunctional or hybrid devices. First, embodiments of the second broad aspect include the elongate puncture member having a rail section that is stiff enough to provide rail for advancing devices, thereby eliminating (making unnecessary) using an anchor wire and the steps of withdrawing the puncture member and advancing the anchor wire. Second, the steerable device is advanced over the puncture member, thereby eliminating the use of a stiff introductory wire and the steps for exchanging the introductory wire and puncture member. Also, embodiments of the second broad aspect include the elongate puncture member being flexible enough to be cooperatively manipulated by the steerable device, steerable sheath 300.

Making reference to FIGS. 7A to 7D, in some embodiments of this broad aspect: step (a) includes advancing the steerable device (e.g. steerable sheath 300) into the right atrium 410 of a heart 400; step (b) includes articulating the steerable device (steerable sheath 300) to manipulate a distal portion of the elongate puncture member (wire 200) for positioning the puncture member; step (c) includes advancing the puncture member (wire 200) to create a puncture in the tissue (atrial septum 422); and step (d) includes advancing dilator 100 over the puncture member (wire 200) through the puncture in the tissue (atrial septum 422). In some embodiments, step (c) further comprises advancing the elongate puncture member into the left atrium. In some embodiments the method further includes a step (e) of withdrawing the steerable device and dilator, whereby the elongate puncture provides a rail for advancing medical devices into the left atrium.

In some embodiments of the second broad aspect, the elongate puncture member is an energy delivery device (e.g. a wire operable to deliver electricity) and puncturing tissue in step (c) comprises delivering energy through the distal end of the energy delivery device to puncture the tissue. In some other embodiments of the second broad aspect, the elongate puncture member is a mechanical wire with a sharp tip and puncturing tissue in step (c) comprises advancing the mechanical wire such that the sharp tip of the mechanical wire punctures the tissue.

A specific embodiment of this broad aspect comprises the steps of: (a) introducing a steerable sheath and a soft dilator into the right atrium; (b) positioning the steerable sheath and the soft dilator such as to be aimed towards the septum; (c) withdrawing the soft dilator and advancing a stiffer dilator; (d) adjusting the steerable sheath to position the stiffer dilator, and an energy delivery device inside the dilator's lumen, substantially adjacent the atrial septum; (e) delivering energy through the distal end of the energy delivery device to puncture the septum; (f) advancing the energy delivery device until a distal tip of the energy delivery device crosses the septum and enters the left atrium wherein the portion of the energy delivery device bridging the right atrium and septum is stiff enough to provide a device-supporting rail to the left atrium; and (g) advancing the stiffer dilator to dilate the puncture.

Some embodiments of this broad aspect include using a soft and a hard dilator, while some alternative embodiments include using a hybrid dilator as described hereinabove.

Details regarding characteristics of the initial broad aspect of an embodiment of a method of the present invention, including (but not limited to) the description of tenting, the use of electricity and the dilator supporting the steerable sheath, also apply to the second broad aspect.

A further broad aspect of the method of accessing a chamber of a patient's heart using a superior access approach is described below. The method comprises the steps of: (a) advancing a steerable device through a patient's vasculature, from a superior approach, into a heart of a patient, the steerable device defining a lumen and containing a dilator within the lumen; (b) articulating the steerable device to manipulate a distal portion of the dilator for positioning the dilator substantially adjacent a tissue; (c) advancing an elongate puncture member, from within a lumen of the dilator, to create a puncture in the tissue; and (d) advancing the dilator over the elongate puncture member through the puncture.

This broad aspect, similar to the first broad aspect mentioned above with respect to a method of the resent invention, also uses a hybrid dilator. The use of the hybrid dilator renders unnecessary the use of a soft dilator for steering and bending, and then changing to a stiffer dilator for crossing tissue, whereby the hybrid dilator reduces the number of steps in the procedure by eliminating the steps of withdrawing a soft dilator and advancing a stiffer (hard) dilator. Also, this broad aspect, similar to the second mentioned above, includes the elongate puncture member having a rail section that is stiff enough to provide rail for advancing devices, thereby eliminating (making unnecessary) the use of an anchor wire and the steps of exchanging the puncture member and anchor wire. Thus, this broad aspect includes embodiments of both hybrid devices described hereinabove.

Making reference again to FIGS. 7A-7D, some embodiments of the method comprises the steps of: (a) advancing a steerable sheath 300 containing dilator 100 within a lumen of steerable sheath 300, from a superior approach, into a heart 400 of a patient; (b) articulating the steerable sheath 300 to manipulate a distal portion of dilator 100 for positioning the dilator substantially adjacent atrial septum 422; (c) advancing an elongate puncture member (wire 200), from a lumen of dilator 100, to create a puncture in atrial septum 422; and (d) advancing dilator 100 over wire 200 and through the puncture.

Similar to the previous broad aspects, step (c) comprises advancing the elongate puncture member to enter into the left atrium. In some embodiments of the third broad aspect, the method further includes a step (e) of withdrawing the steerable device and dilator to thereby provide a rail for advancing medical devices into the left atrium.

In some embodiments of the third broad aspect, the elongate puncture member is an energy delivery device and puncturing the tissue in step (c) comprises delivering energy through a distal end of the energy delivery device to puncture the tissue. In some other embodiments of the third broad aspect, the elongate puncture member is a mechanical wire with a sharp tip and puncturing the tissue in step (c) comprises advancing the mechanical wire such that the sharp tip of the mechanical wire punctures the tissue.

A specific embodiment of this third broad aspect comprises the steps of: (a) introducing a steerable sheath and a dilator into the right atrium; (b) positioning the steerable sheath and the dilator such as to be aimed towards the septum wherein the portion of the dilator shaft within the steerable sheath is flexible enough to be cooperatively steered by the sheath; (c) adjusting the steerable sheath to cooperatively position the dilator, and an energy delivery device inside the dilator's lumen, substantially adjacent the atrial septum; (d) delivering energy through the distal end of the energy delivery device to puncture the septum; (e) advancing the energy delivery device until a distal portion tip of the energy delivery device bridges (crosses) the septum and enters the left atrium wherein the distal portion of the energy delivery device bridging the right atrium and septum is stiff enough to provide a device-supporting rail to the left atrium; and (f) advancing the dilator whereby a shape-retaining (i.e. hard) tip section of the dilator dilates the puncture.

Details regarding the earlier broad aspects, including (but not limited to) the description of tenting, the use of electricity and the dilator supporting the steerable sheath, also apply to this third broad aspect.

A fourth broad aspect of the invention is described below. Making reference to FIGS. 7A to 7B, it is a method of accessing a chamber of a patient's heart using a superior access approach. The method comprises the steps of: (a) advancing an energy delivery device from an access site superior to the heart, through a superior vena cava and into a right atrium; (b) adjusting/articulating/manipulating a steerable device to position the energy delivery device substantially adjacent a septum of the heart; (c) delivering energy through a distal end of the energy delivery device to puncture the septum; (d) advancing the energy delivery device into a left atrium; and (e) advancing a dilator over the energy delivery device whereby the dilator dilates the puncture.

The fourth broad aspect also relates to the concept of reducing or minimizing the number of steps in a procedure by using hybrid devices. Embodiments of the fourth broad aspect include using an energy delivery device (wire 200) having a rail section that is stiff enough to provide rail for advancing devices, thereby making unnecessary using an anchor wire and eliminating the steps of withdrawing the energy delivery device and advancing the anchor wire.

Some embodiments of this aspect further comprise a step (f) of withdrawing the steerable device (steerable sheath 300) and the dilator 100, after which the portion of the energy delivery device bridging the right atrium and septum is stiff enough to provide a device-supporting rail to the left atrium for advancing medical devices into the left atrium.

Some embodiments of the fourth broad aspect include using a soft and a hard dilator, while some alternative embodiments include using a hybrid dilator.

In some embodiments of the fourth broad aspect, the access site is at a left subclavian vein 420. In some other embodiments, the access site is at a right subclavian vein. In yet some further embodiments, the access site is at a jugular vein.

Details regarding the first broad aspect, including (but not limited to) the description of tenting, the use of electricity and the dilator supporting the steerable sheath, also apply to the fourth broad aspect.

Thus, as described above, disclosed herein are several embodiments of a method of providing access for medical devices to a specified tissue site, such as the left side of the heart from a particular access site, such as superior access site. The method comprises using one or more hybrid devices for performing multiple steps of a medical procedure to thereby reduce and/or minimize the number of device exchanges. Some of the methods include puncturing the left side of the heart using an energy delivery device sufficiently flexible so as to be advanced from a superior approach and using the energy delivery device as a rail for advancing other instruments thereupon, thereby providing a means of support for advancing instrumentation through to the left side of the heart.

FURTHER EXAMPLES

Example 1. A multi-function guidewire for a accessing a heart including a septum, the multi-function guidewire comprising: a rail section sufficiently stiff to act as rail and flexible enough to enable access to a septum from any approach; a distal section which is generally curved and distal of the rail section; and an active tip at a distal end of the distal section, the active tip operable to deliver energy for puncturing the septum to define a puncture site; the distal section being configured to form a coil whereby it anchors the multi-function guidewire beyond the puncture site when the distal section is advanced beyond the septum.

Example 2. The multi-function guidewire of example 1, wherein the rail is sufficiently flexible to enable access to the septum from an inferior approach and/or a superior approach.

Example 3. The multi-function guidewire of example 1, wherein the rail section has a maximum outer diameter of about 1.1 mm and a minimum outer diameter of about 0.58 mm, or more particularly, an outer diameter of about 0.86 mm at its proximal end and about 0.72 mm at its distal end.

Example 4. The multi-function guidewire of example 1, further comprising a metal wire, wherein the metal wire of a proximal curved portion of the proximal section has an outer diameter of about 0.13 to about 0.64 mm or, more specifically, an outer diameter of about 0.38 mm.

Example 5. The multi-function guidewire of example 1, wherein the distal section is sized and configured to anchor a distal end of the multi-function guidewire in an atrium without accidentally being advanced into openings adjacent the left atrium such as a left pulmonary vein or a mitral valve.

Example 6. The multi-function guidewire of example 1, wherein the rail section has a maximum elasticity of about 2100 N/m and a minimum elasticity of about 100 N/m.

Example 7. The multi-function guidewire of example 1, wherein a distal curved portion of the distal section has a maximum elasticity of about 550 N/m and a minimum elasticity of about 1 N/m.

Example 8. The multi-function guidewire of example 1, wherein the distal section comprises a spiral-shaped coil traversing a curve of about 630°.

Example 9. The multi-function guidewire of example 8, wherein a diameter of an inner curve of the coil is between about 6 mm to about 30 mm or, more specifically, about 10 mm.

Example 10. The multi-function guidewire of example 8, wherein a diameter of an outer curve of the coil is between about 20 mm to about 40 mm or, more specifically, about 22 mm.

Example 11. The multi-function guidewire of example 1, wherein a diameter of the guidewire decreases distally along a distal curved portion of the distal section.

Example 12. The multi-function guidewire of example 11, wherein an outer diameter of the guidewire at a proximal end of the distal curved portion is between about 0.72 mm to about 0.86 mm, and an outer diameter at a distal end of the distal curved portion is between about 0.59 mm to about 0.72 mm.

Example 13. The multi-function guidewire of example 1, wherein the distal section further comprises a helical coil, the helical coil having a length of between about 15 mm to about 100 mm or, more particularly, about 30 mm.

Example 14. The multi-function guidewire of example 13, wherein the helical coil is comprised of platinum and tungsten or, more particularly, wherein the helical coil comprises about 8% tungsten.

Example 15. The multi-function guidewire of example 1, wherein the active tip is comprised of platinum and iridium or, more particularly, wherein the active tip is comprised of platinum with 10% iridium.

Example 16. The multi-function guidewire of example 1, wherein the proximal section is biased to a curved configuration, the curved configuration being selected from the group consisting of a spiral-shaped coil and a constant diameter coil.

Example 17. The multi-function guidewire of example 1, wherein an outer diameter of the guidewire at the proximal section is between about 0.35 mm to about 0.86 mm or, more particularly, about 0.6 mm.

Example 18. A dilator for use with a steerable sheath to access a region of tissue within a patient's body, the steerable sheath defining a lumen there-through for receiving the dilator and having a range of deflection angles, the dilator comprising: a rigid distal end region; and a flexible intermediate region terminating at the distal end region; the dilator being configured for use in conjunction with the steerable sheath such that a location of the flexible intermediate region corresponds to a location of a region of the steerable sheath that is amenable to deflection; and the rigid distal end region having a rigidity greater than the flexible intermediate region to enable the dilator to advance through tissue.

Example 19. The dilator of example 18, wherein the dilator comprises a substantially straight dilator.

Example 20. The dilator of example 18, wherein the distal end region comprises a rigid polymer and the intermediate region comprises a flexible polymer.

Example 21. The dilator of example 20, wherein the rigid distal end region is formed from High Density Polyethylene and the flexible intermediate region is formed from Low Density Polyethylene.

Example 22. The dilator of example 18, wherein the flexible intermediate region has a length of between about 7 cm to about 17 cm or, more particularly, about 15 cm.

Example 23. The dilator of example 18, wherein the rigid distal end region has a length of between about 0.4 cm to about 4.0 cm or, more particularly, between about 0.5 cm to about 1.0 cm or, even more particularly, between about 0.6 cm to about 0.7 cm.

Example 24. The dilator of example 18, wherein the dilator defines a taper.

Example 25. The dilator of example 24, wherein the rigid distal end region forms a part of the taper.

Example 26. The dilator of example 25, wherein the taper has a length of about 1 cm.

Example 27. The dilator of example 18, wherein the rigid distal end region has a length of between about 2.5% to about 60% of a length of said flexible intermediate region.

Example 28. The dilator of example 18, wherein the dilator further comprises a proximal region extending proximally from the flexible intermediate region, the proximal region having a rigidity greater than the flexible intermediate region.

Example 29. The dilator of example 28, wherein the distal end region and the proximal region have a rigidity that is substantially equal.

Example 30. The dilator of example 29, wherein the distal end region and the proximal region are formed from a rigid polymer and wherein the intermediate region is formed from a flexible polymer.

Example 31. The dilator of example 30, wherein the distal end region and the proximal region are formed from High Density Polyethylene, and wherein the flexible intermediate region is formed from Low Density Polyethylene.

Example 32. The dilator of example 29, wherein the rigidity of each of the distal end region and the proximal region is equal to about 0.8 GPa and wherein the rigidity of the flexible intermediate region is equal to about 0.3 Gpa.

Example 33. The dilator of example 18, wherein the steerable sheath is actuatable to define a curve.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A medical device for creating a transseptal puncture within a patient's heart, the medical device comprising:

a multi-function guidewire having a proximal section, a distal section including an electrode, and a rail section between the proximal and distal sections;

the electrode operable to deliver energy to aid the creation of a puncture through a septum of the patient's heart; and the rail section being configured to both act as a rail for supporting installation of one or more treatment tools thereupon as well as to be maneuverable for enabling access to the heart septum by the guidewire;

wherein the distal section comprises a curved portion and a straight portion, the straight portion being distal to the curved portion;

wherein a stiffness of the guidewire at a region in the straight portion is greater than a stiffness of the guidewire at a region in the curved portion;

wherein the distal section is configured to automatically form a coil or a J-shape in a deployed state for anchoring the distal section.

2. The medical device of claim 1, wherein a stiffness of the guidewire at a region in the rail section is greater than the stiffness of the guidewire at the region in the distal section curved portion.

3. The medical device of claim 2, wherein a stiffness of the guidewire at a region in the proximal section is less than the stiffness of the guidewire at the region in the rail section.

4. The medical device of claim 1, further comprising a radiofrequency (RF) generator for supplying the energy to the electrode.

5. The medical device of claim 4, wherein the supply of the energy is controlled through the use of a push button in communication with the generator.

6. The medical device of claim 1, further comprising a radiopaque marker positioned on the distal section of the guidewire.

7. The medical device of claim 6, wherein the radiopaque marker is a helical coil surrounding the guidewire at the distal section.

8. A medical device for creating a transseptal puncture within a patient's heart, the medical device comprising:

a multi-function guidewire having at least a rail section and a distal section, wherein the rail section is proximal of the distal section, and wherein the distal section includes an electrode having an atraumatic tip;

the electrode operable to deliver energy to aid the creation of a puncture through a septum of the patient's heart; and the rail section being configured to both act as a rail for supporting installation of one or more treatment tools thereupon as well as to be maneuverable for enabling access to the heart septum by the guidewire;

wherein the distal section comprises a curved portion and a straight portion, the straight portion being distal to the curved portion;

wherein at least part of the straight portion has a first stiffness and at least part of the curved portion has a second stiffness, and the first stiffness is greater than the second stiffness.

9. The medical device of claim 8, wherein at least part of the rail section of the guidewire has a third stiffness greater than the second stiffness.

10. The medical device of claim 8, wherein at least part of the rail section of the guidewire has a fourth stiffness greater than the first stiffness.

11. The medical device of claim 8, wherein the rail section of the guidewire is sufficiently stiff to enable puncturing the septum of the patient's heart from a superior approach.

12. The medical device of claim 8, wherein the rail section of the guidewire is sufficiently stiff to enable puncturing the septum of the patient's heart from an inferior approach.

13. The medical device of claim 8, wherein the guidewire is configured for electrical communication with a radiofrequency (RF) generator for supplying the energy to the electrode.

\* \* \* \* \*